(12) United States Patent
Mathis et al.

(10) Patent No.: US 10,034,999 B2
(45) Date of Patent: Jul. 31, 2018

(54) STEERABLE DEVICE FOR ACCESSING A TARGET SITE AND METHODS

(71) Applicant: PneumRx, Inc., Santa Clara, CA (US)

(72) Inventors: Mark Mathis, Fremont, CA (US);
David Thompson, San Jose, CA (US);
Bruce Addis, Redwood City, CA (US);
David F. Yankelevitz, Brooklyn, NY (US)

(73) Assignee: PneumRx, Inc., Santa Clara, CA (US)

( * ) Notice: Subject to any disclaimer, the term of this patent is extended or adjusted under 35 U.S.C. 154(b) by 182 days.

(21) Appl. No.: 14/814,349

(22) Filed: Jul. 30, 2015

(65) Prior Publication Data

US 2015/0328435 A1    Nov. 19, 2015

Related U.S. Application Data

(63) Continuation of application No. 11/286,445, filed on Nov. 23, 2005, now Pat. No. 9,125,639.
(Continued)

(51) Int. Cl.
*A61B 5/00* (2006.01)
*A61M 25/01* (2006.01)
(Continued)

(52) U.S. Cl.
CPC ..... *A61M 25/0147* (2013.01); *A61B 10/0275* (2013.01); *A61B 10/04* (2013.01);
(Continued)

(58) Field of Classification Search
CPC .. A61B 10/04; A61B 2010/045; A61M 25/09; A61M 2025/091; A61M 2025/09125; A61M 25/00; A61M 25/0147
See application file for complete search history.

(56) References Cited

U.S. PATENT DOCUMENTS

| 3,559,652 A | 2/1971 | Banitt et al. |
| 4,013,080 A | 3/1977 | Froning |

(Continued)

FOREIGN PATENT DOCUMENTS

| FR | 2840796 | 12/2003 |
| GB | 2324729 A | 1/2002 |

(Continued)

OTHER PUBLICATIONS

Hermanson, Greg T. Bioconjugate Techniques. San Diego: Academic Press, Inc. 1996. (Table of contents only), 3 pages.
(Continued)

*Primary Examiner* — Max Hindenburg
(74) *Attorney, Agent, or Firm* — Kilpatrick, Townsend & Stockton LLP

(57) ABSTRACT

A variety of steerable needles, lancets, trocars, stylets, cannulas and systems are provided for examining, diagnosing, treating, or removing tissue from a patient. The steerable needles, trocars, stylets, cannulas and systems also provide a platform for delivery of target materials, such as therapeutics, biologics, polymes, glues, etc., to a target site. An embodiment of the invention includes a steerable device for use in accessing target site in a patient comprising: a steerable member adapted to penetrate tissue; and a steering mechanism adapted to be operated by a user to apply a bending force to bend the steerable member to access the target site.

12 Claims, 28 Drawing Sheets

Related U.S. Application Data

(60) Provisional application No. 60/630,803, filed on Nov. 23, 2004.

(51) Int. Cl.

| | | |
|---|---|---|
| *A61B 18/14* | (2006.01) | |
| *A61F 7/00* | (2006.01) | |
| *A61B 17/34* | (2006.01) | |
| *A61B 10/02* | (2006.01) | |
| *A61B 10/04* | (2006.01) | |
| *A61B 17/29* | (2006.01) | |
| *A61B 17/00* | (2006.01) | |
| *A61M 25/00* | (2006.01) | |

(52) U.S. Cl.
CPC ...... *A61B 17/3403* (2013.01); *A61B 17/3417* (2013.01); *A61B 17/3468* (2013.01); *A61B 17/3478* (2013.01); *A61B 18/1477* (2013.01); *A61B 18/1492* (2013.01); *A61F 7/00* (2013.01); *A61B 17/2909* (2013.01); *A61B 2010/045* (2013.01); *A61B 2017/003* (2013.01); *A61B 2017/00867* (2013.01); *A61B 2017/2927* (2013.01); *A61B 2017/3405* (2013.01); *A61M 25/00* (2013.01)

(56) References Cited

U.S. PATENT DOCUMENTS

| | | | |
|---|---|---|---|
| 4,153,058 A | | 5/1979 | Nehme |
| 4,233,984 A | | 11/1980 | Walling |
| 4,479,792 A | | 10/1984 | Lazarus et al. |
| 4,532,935 A | | 8/1985 | Wang |
| 4,702,260 A | | 10/1987 | Wang |
| 4,739,760 A | | 4/1988 | Chin et al. |
| 4,766,906 A | | 8/1988 | Wang |
| 4,769,017 A | | 9/1988 | Fath et al. |
| 4,880,015 A | | 11/1989 | Nierman |
| 5,056,529 A | | 10/1991 | de Groot |
| 5,084,012 A | | 1/1992 | Kelman |
| 5,108,368 A | | 4/1992 | Hammerslag et al. |
| 5,165,420 A | | 11/1992 | Strickland |
| 5,186,167 A | | 2/1993 | Kolobow |
| 5,190,546 A | | 3/1993 | Jervis |
| 5,219,895 A | | 6/1993 | Kelman |
| 5,240,011 A | | 8/1993 | Assa |
| 5,261,889 A | | 11/1993 | Laine et al. |
| 5,285,795 A | * | 2/1994 | Ryan ............... A61B 17/32002 600/562 |
| 5,312,329 A | | 5/1994 | Beaty et al. |
| 5,312,331 A | | 5/1994 | Knoepfler |
| 5,315,992 A | | 5/1994 | Dalton |
| 5,334,183 A | | 8/1994 | Wuchinich |
| 5,354,287 A | | 10/1994 | Wacks |
| 5,423,830 A | | 6/1995 | Schneebaum et al. |
| 5,484,401 A | | 1/1996 | Rodriguez et al. |
| 5,514,536 A | | 5/1996 | Taylor |
| 5,526,821 A | | 6/1996 | Jamshidi |
| 5,531,684 A | * | 7/1996 | Ensminger ........ A61M 39/0208 604/175 |
| 5,549,904 A | | 8/1996 | Juergensen et al. |
| 5,573,010 A | | 11/1996 | Pflugbeil |
| 5,599,294 A | | 2/1997 | Edwards et al. |
| 5,599,305 A | | 2/1997 | Hermann et al. |
| 5,660,175 A | | 8/1997 | Dayal |
| 5,660,185 A | | 8/1997 | Shmulewitz et al. |
| 5,697,365 A | | 12/1997 | Pel |
| 5,735,264 A | | 4/1998 | Siczek et al. |
| 5,736,132 A | | 4/1998 | Juergensen et al. |
| 5,750,657 A | | 5/1998 | Edwardson et al. |
| 5,846,235 A | | 12/1998 | Pasricha et al. |
| 5,916,210 A | | 6/1999 | Winston |
| 5,916,212 A | | 6/1999 | Baust et al. |
| 5,938,635 A | | 8/1999 | Kuhle |
| 5,954,636 A | | 9/1999 | Schwartz et al. |
| 5,957,919 A | | 9/1999 | Laufer |
| 5,964,770 A | | 10/1999 | Flomenblit et al. |
| 5,972,026 A | | 10/1999 | Laufer et al. |
| 5,978,697 A | | 11/1999 | Maytal et al. |
| 6,010,449 A | | 1/2000 | Selmon et al. |
| 6,066,090 A | | 5/2000 | Yoon |
| 6,080,113 A | | 6/2000 | Heneveld et al. |
| 6,083,255 A | | 7/2000 | Laufer et al. |
| 6,126,633 A | | 10/2000 | Kaji et al. |
| 6,258,100 B1 | | 7/2001 | Alferness et al. |
| 6,267,732 B1 | | 7/2001 | Heneveld et al. |
| 6,273,907 B1 | | 8/2001 | Laufer |
| 6,283,988 B1 | | 9/2001 | Laufer et al. |
| 6,283,989 B1 | | 9/2001 | Laufer et al. |
| 6,287,290 B1 | | 9/2001 | Perkins et al. |
| 6,287,304 B1 | | 9/2001 | Eggers et al. |
| 6,293,951 B1 | | 9/2001 | Alferness et al. |
| 6,299,633 B1 | | 10/2001 | Laufer |
| 6,310,166 B1 | | 10/2001 | Hickey et al. |
| 6,312,428 B1 | | 11/2001 | Eggers et al. |
| 6,315,737 B1 | | 11/2001 | Skinner |
| 6,328,689 B1 | | 12/2001 | Gonzalez et al. |
| 6,328,701 B1 | | 12/2001 | Terwilliger |
| 6,352,503 B1 | | 3/2002 | Matsui et al. |
| 6,379,373 B1 | | 4/2002 | Sawhney et al. |
| 6,387,044 B1 | | 5/2002 | Tachibana et al. |
| 6,390,967 B1 | | 5/2002 | Forman et al. |
| 6,398,775 B1 | | 6/2002 | Perkins et al. |
| 6,402,701 B1 | | 6/2002 | Kaplan et al. |
| 6,402,754 B1 | | 6/2002 | Gonzalez |
| 6,411,852 B1 | | 6/2002 | Danek et al. |
| 6,416,554 B1 | | 7/2002 | Alferness et al. |
| 6,443,944 B1 | | 9/2002 | Doshi et al. |
| 6,478,730 B1 | | 11/2002 | Bala et al. |
| 6,485,407 B2 | | 11/2002 | Alferness et al. |
| 6,485,436 B1 | | 11/2002 | Truckai et al. |
| 6,488,673 B1 | | 12/2002 | Laufer et al. |
| 6,491,706 B1 | | 12/2002 | Alferness et al. |
| 6,494,844 B1 | | 12/2002 | Van Bladel et al. |
| 6,494,897 B2 | | 12/2002 | Sterman et al. |
| 6,509,031 B1 | | 1/2003 | Miller et al. |
| 6,514,290 B1 | | 2/2003 | Loomas |
| 6,514,522 B2 | | 2/2003 | Domb |
| 6,527,761 B1 | | 3/2003 | Soltesz et al. |
| 6,537,195 B2 | | 3/2003 | Forman |
| 6,537,314 B2 | | 3/2003 | Langberg et al. |
| 6,540,694 B1 | | 4/2003 | Van Bladel et al. |
| 6,540,716 B1 | | 4/2003 | Holm |
| 6,549,800 B1 | | 4/2003 | Atalar et al. |
| 6,551,255 B2 | | 4/2003 | Van Bladel et al. |
| 6,551,302 B1 | | 4/2003 | Rosinko et al. |
| 6,552,172 B2 | | 4/2003 | Marx et al. |
| 6,554,794 B1 | | 4/2003 | Mueller et al. |
| 6,558,337 B2 | | 5/2003 | Dvorak et al. |
| 6,568,387 B2 | | 5/2003 | Davenport et al. |
| 6,569,166 B2 | | 5/2003 | Gonzalez |
| 6,577,893 B1 | | 6/2003 | Besson et al. |
| 6,585,639 B1 | | 7/2003 | Kotmel et al. |
| 6,589,161 B2 | | 7/2003 | Corcoran |
| 6,592,559 B1 | | 7/2003 | Pakter et al. |
| 6,592,594 B2 | | 7/2003 | Rimbaugh et al. |
| 6,595,979 B1 | * | 7/2003 | Epstein ............... A61M 5/1456 604/506 |
| 6,599,311 B1 | | 7/2003 | Biggs et al. |
| 6,610,043 B1 | | 8/2003 | Ingenito |
| 6,622,731 B2 | | 9/2003 | Daniel et al. |
| 6,629,951 B2 | | 10/2003 | Laufer et al. |
| 6,632,222 B1 | | 10/2003 | Edwards et al. |
| 6,632,239 B2 | | 10/2003 | Snyder et al. |
| 6,632,243 B1 | | 10/2003 | Zadno-Azizi et al. |
| 6,634,363 B1 | | 10/2003 | Danek et al. |
| 6,638,275 B1 | | 10/2003 | McGaffigan et al. |
| 6,641,553 B1 | * | 11/2003 | Chee ............... A61B 17/32037 604/68 |
| 6,652,516 B1 | | 11/2003 | Gough |
| 6,652,520 B2 | | 11/2003 | Moorman et al. |
| 6,653,525 B2 | | 11/2003 | Ingenito et al. |
| 6,663,624 B2 | | 12/2003 | Edwards et al. |

(56) References Cited

U.S. PATENT DOCUMENTS

| | | |
|---|---|---|
| 6,679,264 B1 | 1/2004 | Deem et al. |
| 6,682,520 B2 | 1/2004 | Ingenito |
| 6,685,626 B2 | 2/2004 | Wironen |
| 6,689,072 B2 | 2/2004 | Kaplan et al. |
| 6,690,976 B2 | 2/2004 | Fenn et al. |
| 6,692,494 B1 | 2/2004 | Cooper et al. |
| 6,694,979 B2 | 2/2004 | Deem et al. |
| 6,695,791 B2 | 2/2004 | Gonzalez |
| 6,709,401 B2 | 3/2004 | Perkins et al. |
| 6,709,408 B2 | 3/2004 | Fisher |
| 6,709,456 B2 | 3/2004 | Langberg et al. |
| 6,712,812 B2 | 3/2004 | Roschak et al. |
| 6,716,180 B2 | 4/2004 | Fontenot |
| 6,723,095 B2 | 4/2004 | Hammerslag |
| 6,730,044 B2 | 5/2004 | Stephens et al. |
| 6,736,822 B2 | 5/2004 | McClellan et al. |
| 6,752,767 B2 | 6/2004 | Turovskiy et al. |
| 6,752,812 B1 | 6/2004 | Truwit |
| 6,758,824 B1 | 7/2004 | Miller et al. |
| 6,768,425 B2 | 7/2004 | Flaherty et al. |
| 6,770,066 B1 | 8/2004 | Weaver et al. |
| 6,770,070 B1 | 8/2004 | Balbierz |
| 6,789,545 B2 | 9/2004 | Littrup et al. |
| 6,790,172 B2 | 9/2004 | Alferness et al. |
| 6,790,185 B1 | 9/2004 | Fisher et al. |
| 6,797,001 B2 | 9/2004 | Mathis et al. |
| 6,807,446 B2 | 10/2004 | Fenn et al. |
| 6,808,525 B2 | 10/2004 | Latterell et al. |
| 6,817,973 B2 | 11/2004 | Merril et al. |
| 6,825,091 B2 | 11/2004 | Bae et al. |
| 6,827,086 B2 | 12/2004 | Shuman |
| 6,830,756 B2 | 12/2004 | Hnojewyj |
| 6,840,243 B2 | 1/2005 | Deem et al. |
| 6,840,948 B2 | 1/2005 | Albrecht et al. |
| 6,840,952 B2 | 1/2005 | Saker et al. |
| 6,843,767 B2 | 1/2005 | Corcoran et al. |
| 6,849,262 B2 | 2/2005 | Ollerenshaw et al. |
| 6,852,108 B2 | 2/2005 | Barry et al. |
| 6,860,847 B2 | 3/2005 | Alferness et al. |
| 6,863,676 B2 | 3/2005 | Lee et al. |
| 6,875,209 B2 | 4/2005 | Zvuloni et al. |
| 6,878,106 B1 | 4/2005 | Herrmann |
| 6,878,141 B1 | 4/2005 | Perkins et al. |
| 6,886,558 B2 | 5/2005 | Tanaka |
| 6,901,927 B2 | 6/2005 | Deem et al. |
| 6,902,526 B2 | 6/2005 | Katzman |
| 6,902,536 B2 | 6/2005 | Manna et al. |
| 6,904,909 B2 | 6/2005 | Andreas et al. |
| 6,908,440 B2 | 6/2005 | Fisher |
| 6,918,881 B2 | 7/2005 | Miller et al. |
| 6,936,014 B2 | 8/2005 | Vetter et al. |
| 6,942,627 B2 | 9/2005 | Huitema |
| 6,945,942 B2 | 9/2005 | Van Bladel et al. |
| 6,962,587 B2 | 11/2005 | Johnson et al. |
| 6,964,662 B2 | 11/2005 | Kidooka |
| 6,967,673 B2 | 11/2005 | Ozawa et al. |
| 7,037,290 B2 | 5/2006 | Gardeski et al. |
| 7,056,314 B1 | 6/2006 | Florio et al. |
| 7,077,842 B1 * | 7/2006 | Cosman ............... A61B 18/148 128/898 |
| 7,169,147 B2 * | 1/2007 | Nosel ................... A61B 18/149 600/104 |
| 7,351,202 B2 * | 4/2008 | Long .................. A61B 1/00133 600/104 |
| 7,967,830 B2 * | 6/2011 | Ayala ..................... A61B 1/018 604/103.04 |
| 8,517,923 B2 * | 8/2013 | Belson .................. A61B 1/0051 600/114 |
| RE45,638 E * | 8/2015 | Tartaglia ............ A61B 17/3207 |
| 2002/0007831 A1 | 1/2002 | Davenport et al. |
| 2002/0026188 A1 | 2/2002 | Balbierz et al. |
| 2002/0042564 A1 | 4/2002 | Cooper et al. |
| 2002/0042565 A1 | 4/2002 | Cooper et al. |
| 2002/0062120 A1 | 5/2002 | Perkins et al. |
| 2002/0077593 A1 | 6/2002 | Perkins et al. |
| 2002/0091379 A1 | 7/2002 | Danek et al. |
| 2002/0111620 A1 | 8/2002 | Cooper et al. |
| 2002/0112729 A1 | 8/2002 | DeVore et al. |
| 2002/0128647 A1 | 9/2002 | Roschak et al. |
| 2002/0138074 A1 | 9/2002 | Keast et al. |
| 2002/0161399 A1 | 10/2002 | Cruise et al. |
| 2002/0176893 A1 | 11/2002 | Wironen et al. |
| 2002/0183244 A1 | 12/2002 | Ollerenshaw et al. |
| 2002/0183838 A1 | 12/2002 | Liddicoat et al. |
| 2002/0188171 A1 | 12/2002 | Alferness et al. |
| 2003/0018318 A1 | 1/2003 | Melsky |
| 2003/0040743 A1 | 2/2003 | Cosman et al. |
| 2003/0070676 A1 | 4/2003 | Cooper et al. |
| 2003/0070682 A1 | 4/2003 | Wilson et al. |
| 2003/0070683 A1 | 4/2003 | Deem et al. |
| 2003/0075170 A1 | 4/2003 | Deem et al. |
| 2003/0083671 A1 | 5/2003 | Rimbaugh et al. |
| 2003/0100921 A1 | 5/2003 | Addis et al. |
| 2003/0109866 A1 | 6/2003 | Edwards et al. |
| 2003/0127090 A1 | 7/2003 | Gifford et al. |
| 2003/0130657 A1 | 7/2003 | Tom et al. |
| 2003/0154988 A1 | 8/2003 | DeVore et al. |
| 2003/0158515 A1 | 8/2003 | Gonzalez et al. |
| 2003/0159700 A1 | 8/2003 | Laufer et al. |
| 2003/0181356 A1 | 9/2003 | Ingenito |
| 2003/0181922 A1 | 9/2003 | Alferness |
| 2003/0183235 A1 | 10/2003 | Rimbaugh et al. |
| 2003/0191496 A1 | 10/2003 | Edwards et al. |
| 2003/0195385 A1 | 10/2003 | DeVore |
| 2003/0195511 A1 | 10/2003 | Barry |
| 2003/0212337 A1 | 11/2003 | Sirokman |
| 2003/0212412 A1 | 11/2003 | Dillard et al. |
| 2003/0233099 A1 | 12/2003 | Danaek et al. |
| 2004/0010209 A1 | 1/2004 | Sirokman |
| 2004/0010289 A1 | 1/2004 | Biggs et al. |
| 2004/0024356 A1 | 2/2004 | Tanaka |
| 2004/0030262 A1 | 2/2004 | Fisher et al. |
| 2004/0031494 A1 | 2/2004 | Danek et al. |
| 2004/0038868 A1 | 2/2004 | Ingenito |
| 2004/0040555 A1 | 3/2004 | Tanaka |
| 2004/0049187 A1 | 3/2004 | Burnett et al. |
| 2004/0052850 A1 | 3/2004 | Schankereli |
| 2004/0055606 A1 | 3/2004 | Hendricksen et al. |
| 2004/0059263 A1 | 3/2004 | DeVore et al. |
| 2004/0063613 A1 | 4/2004 | Rolke et al. |
| 2004/0072756 A1 | 4/2004 | Wilkie et al. |
| 2004/0073155 A1 | 4/2004 | Laufer et al. |
| 2004/0073191 A1 | 4/2004 | Soltesz et al. |
| 2004/0073201 A1 | 4/2004 | Cooper et al. |
| 2004/0073241 A1 | 4/2004 | Barry et al. |
| 2004/0078054 A1 | 4/2004 | Biggs et al. |
| 2004/0081676 A1 | 4/2004 | Schankereli et al. |
| 2004/0120849 A1 | 6/2004 | Stewart et al. |
| 2004/0133168 A1 | 7/2004 | Salcudean et al. |
| 2004/0158228 A1 | 8/2004 | Perkins |
| 2004/0172058 A1 | 9/2004 | Edwards et al. |
| 2004/0176801 A1 | 9/2004 | Edwards et al. |
| 2004/0210248 A1 | 10/2004 | Gordon et al. |
| 2004/0211434 A1 | 10/2004 | Loomas et al. |
| 2004/0215139 A1 | 10/2004 | Cohen |
| 2004/0220556 A1 | 11/2004 | Cooper et al. |
| 2004/0225254 A1 | 11/2004 | Tanaka et al. |
| 2004/0231674 A1 | 11/2004 | Tanaka |
| 2004/0234575 A1 | 11/2004 | Horres et al. |
| 2004/0237966 A1 | 12/2004 | Tanaka |
| 2004/0244802 A1 | 12/2004 | Tanaka |
| 2004/0244803 A1 | 12/2004 | Tanaka |
| 2005/0004599 A1 | 1/2005 | McNally-Heintzelman et al. |
| 2005/0015106 A1 | 1/2005 | Perkins et al. |
| 2005/0043751 A1 | 2/2005 | Phan et al. |
| 2005/0043752 A1 | 2/2005 | Phan et al. |
| 2005/0049615 A1 | 3/2005 | Cooper et al. |
| 2005/0060041 A1 | 3/2005 | Phan et al. |
| 2005/0060042 A1 | 3/2005 | Phan et al. |
| 2005/0061322 A1 | 3/2005 | Freitag |
| 2005/0080356 A1 | 4/2005 | Dapolito et al. |
| 2005/0085801 A1 | 4/2005 | Cooper et al. |
| 2005/0096529 A1 | 5/2005 | Cooper et al. |

(56) References Cited

U.S. PATENT DOCUMENTS

| | | |
|---|---|---|
| 2005/0101984 A1 | 5/2005 | Chanduszko et al. |
| 2005/0107783 A1 | 5/2005 | Tom et al. |
| 2005/0281739 A1 | 12/2005 | Gong et al. |
| 2005/0281740 A1 | 12/2005 | Gong et al. |
| 2005/0281796 A1 | 12/2005 | Gong et al. |
| 2005/0281797 A1 | 12/2005 | Gong et al. |
| 2005/0281798 A1 | 12/2005 | Gong et al. |
| 2005/0281799 A1 | 12/2005 | Gong et al. |
| 2005/0281800 A1 | 12/2005 | Gong et al. |
| 2005/0281801 A1 | 12/2005 | Gong et al. |
| 2005/0281802 A1 | 12/2005 | Gong et al. |
| 2005/0282748 A1 | 12/2005 | Gong et al. |
| 2005/0288549 A1 | 12/2005 | Mathis |
| 2005/0288550 A1 | 12/2005 | Mathis |
| 2005/0288684 A1 | 12/2005 | Aronson et al. |
| 2005/0288702 A1 | 12/2005 | McGurk et al. |
| 2006/0004400 A1 | 1/2006 | McGurk et al. |
| 2006/0009748 A1 | 1/2006 | Mathis |
| 2006/0009801 A1 | 1/2006 | McGurk et al. |
| 2006/0025815 A1 | 2/2006 | McGurk et al. |
| 2007/0221230 A1 | 9/2007 | Thompson et al. |

FOREIGN PATENT DOCUMENTS

| | | |
|---|---|---|
| JP | 07-194610 A | 8/1995 |
| WO | 98/48713 A1 | 11/1998 |
| WO | 00/13592 A1 | 3/2000 |
| WO | 01/13839 A1 | 3/2001 |
| WO | 01/70114 A1 | 9/2001 |
| WO | 02/00270 A1 | 1/2002 |
| WO | 02/00275 A1 | 1/2002 |
| WO | 02/02158 A1 | 1/2002 |
| WO | 03/077768 | 9/2003 |
| WO | 2004/062505 A1 | 7/2004 |
| WO | 2004/086977 A1 | 10/2004 |

OTHER PUBLICATIONS

Lam, et al. X-Ray Diagnosis: A Physician's Approach. Singapore: Springer. 1998. (Table of contents only), 6 pages.

Rowe, et al. Handbook of Pharmaceutical Excipients. 4th Edition. London: Pharmaceutical Press. 2003. (Table of contents only), 6 pages.

Slone, et al. Body CT: A Practical Approach. New York: McGraw-Hill. 2000. (Table of contents only), 4 pages.

Stout, et al. X-Ray Structure Determination: A Practical Guide. 2nd Edition. New York: John Wiley & Sons. 1989. (Table of contents only), 9 pages.

The United States Pharmacopeia. 29th Revision. 2006. The United States Pharmacopeia Convention. Rockville, MD. (Table of contents only), 4 pages.

\* cited by examiner

STEERABLE DEVICE FOR ACCESSING A TARGET SITE AND METHODS

CROSS-REFERENCES TO RELATED APPLICATIONS

This application is a continuation of U.S. patent application Ser. No. 11/286,445, filed Nov. 23, 2005, entitled "Steerable device for accessing a target site and method" which claims the benefit of U.S. Provisional Application No. 60/630,803, filed Nov. 23, 2004, entitled "Steerable Biopsy Needle Apparatus and Method" (Mathis et al.) which is incorporated herein by reference in its entirety.

This application also claims the benefit of U.S. Provisional Application No. 60/666,746, filed Mar. 29, 2005, entitled "Steerable Needle System" (Yankelevitz) which is incorporated herein by reference in its entirety.

BACKGROUND OF THE INVENTION

Field of the Invention

This invention relates generally to a design of devices and systems for safely and effectively accessing tissue. The invention provides a device and system that can be easily steered through tissue within a patient from a location outside the patient's body. The system also provides a platform for delivery of materials and devices to a target site or anatomic location within a body.

Description of Related Art

A variety of needles, lancets, trocars, stylets, cannulas, devices and systems for examining, diagnosing, treating, or removing tissue from a patient are known in the art. See, U.S. Pat. No. 4,013,080 entitled Cannula Connector and Director Indicator Means for Injection System (Froning); U.S. Pat. No. 4,769,017 entitled Self-Sealing Infusion Manifold and Catheter Connector (Fath et al); U.S. Pat. No. 5,240,011 entitled Motorized Biopsy Needle Positioner (Assa); U.S. Pat. No. 5,526,821 entitled Biopsy Needle with Sample Retaining Means (Jamshidi); U.S. Pat. No. 5,660,185 entitled Image-Guided Biopsy Apparatus with Enhanced Imaging and Methods (Shmulewitz); U.S. Pat. No. 5,735,264 entitled Motorized Mammographic Biopsy Apparatus (Siczek et al); U.S. Pat. No. 6,315,737 B1 entitled Biopsy Needle for a Biopsy Instrument (Skinner); U.S. Pat. No. 6,328,701 B1 entitled Biopsy Needle and Surgical Instrument (Terwilliger); U.S. Pat. No. 6,402,701 B1 entitled Biopsy Needle Instrument (Kaplan); U.S. Pat. No. 6,464,648 B1 entitled Biopsy Device and Remote Control Device Therefor (Nakamura); U.S. Pat. No. 6,485,436 B1 entitled Pressure-Assisted Biopsy Needle Apparatus and Technique (Truckai et al); U.S. Pat. No. 6,558,337 B2 entitled Positioner for Medical Devices such as Biopsy Needles (Dvorak et al); U.S. Pat. No. 6,709,408 B2 entitled Dual Action Aspiration Biopsy Needle (Fisher); U.S. Pat. No. 6,908,440 B2 entitled Dual Action Aspiration Biopsy Needle (Fisher); and U.S. Pat. No. 6,918,881 B2 entitled Biopsy Needle with Integrated Guide Pin (Miller et al). U.S. Patent Publications US 2004/0133168 A1 entitled Steerable Needle (Salcudean et al.); as well as PCT Publications WO 00/13592 A1 entitled Device for Receiving and Actuating a Biopsy Needle (Heinrich); WO 03/077768 A1 entitled Biopsy Needle and Biopsy Needle Module that Can be Inserted into the Biopsy Device (Heske et al); WO 2004/062505 A1 entitled Flexible Biopsy Needle (Bates et al.); and WO 2004/086977 A1 entitled Coaxial Cannula Provided with a Sealing Element (Reske et al.).

For example, biopsy needles are used in the medical field to remove tissue, cells or fluids from a body for examination and diagnostic testing. Biopsy needles can form part of a biopsy system. Currently, there are three main types of procedures that are used to obtain a biopsy, or tissue sample. First, a surgeon can use a scalpel, or other suitable cutting instrument, to make an incision in a patient that is large enough for the surgeon to access the tissue to be tested. One or more large pieces of a target site, such as a tumor, lesion, cells or fluid, are then removed and tested for malignancy. This procedure is typically performed under general anesthesia.

Another technique, the core tissue biopsy procedure, uses a large bore needle to cut or shear away one or more visible pieces of a tumor or lesion. The pieces of tissue obtained using a large bore needle are visible to the unaided eye and may require further processing to view through a microscope (i.e., due to the size and thickness of the tissue pieces obtained).

Yet another technique is the use of fine needle aspiration (FNA) needles with small bores to obtain tissue samples. A needle is used with a syringe to access the target site. Negative pressure is created in the syringe, and as a result of the pressure difference between the syringe and the mass, cellular material can be drawn into the syringe and removed. Typically, the needle is moved in and out in order to facilitate obtaining enough tissue or material to examine and make a diagnosis.

There are many medical conditions for which a physician might wish to obtain access to a target site or obtain a sample of tissue or material from a patient. For example, pulmonary disorders affect millions of Americans, and many more individuals worldwide, each year. While some pulmonary disorders are chronic (e.g., chronic obstructive pulmonary disease (COPD)), many are acute and deadly. For example, lung cancer is the leading cause of death attributable to cancer for both men and women. More people die of lung cancer, than die of breast, prostate and colon cancer combined. It is estimated that in the United States alone, over 170,000 new cases of lung cancer are diagnosed each year. Of those people diagnosed with lung cancer, the prognosis is grim: 6 of 10 will die within one year of being diagnosed and between 7 and 8 will die within two years of diagnosis.

Most lung cancers start in the lining of the bronchi (plural for bronchus), although lung cancer can start in other parts of the lung as well. Since it generally takes many years for lung cancer to develop, there can be areas of pre-cancerous changes in the lung long before the formation of lung cancer. With currently available technology, the pre-cancerous changes are often not detected because the changes cannot be seen on an x-ray and do not cause symptoms early on that would cause a patient to seek medical attention. It is for this reason that most people with lung cancer are not diagnosed during the critical early stages of the disease.

Taking chest x-rays and checking sputum under a microscope for the appearance of cancer cells had been performed for screening but was found to be unreliable, and thus is not even recommended screening for persons of high risk (e.g., those people who smoke). Recently, spiral CT scanning has shown promise as a potential screening tool for finding lung cancer at an early stage. However, at this juncture it is not known whether the use of spiral CT scans improves the prognosis for long-term survival by increasing the early detection of the disease. Even with a scan indicating the possible presence of pre-cancerous tissue, the ability to take a biopsy for testing is difficult without causing the lungs to collapse, which can result in a required hospital stay.

Each condition where access to tissue for examining or diagnosing a condition, or where obtaining a biopsy would be desirable, presents its own challenges. The, lung, however, presents a useful platform for understanding issues relating to accessing and treating target sites as well as obtaining biopsies.

In the lung, any time a procedure requires an instrument to be inserted through an incision in the chest wall, the pleural layers surrounding the lung are pierced or compromised. As a result of the propensity for transthoracic procedures to cause, for example, pneumothorax, there is a limitation on the outer diameter of the instruments that are used for these procedures. This is a significant drawback for procedures such as percutnaeous transthoracic lung tissue biopsy, where the interventionalist introduces a biopsy needle through the chest wall. Other procedures which are limited when applied to transthoracic procedures include percutaneous transthoracic needle aspiration (PTNA), mediastinoscopy, thoracoscopy and drainage of pleural effusions. Air leaks and bleeding frequently occur either during insertion or removal of the device through the opening in the pleural lining of the chest cavity. Even when using small needles of 19-23 gauge, the incidence of pneumothorax is relatively high, being in the range of 30-40% and the incidence of hemothorax is 25%. Because of the anatomical challenges and physiological mechanics of the lung, accessing the target site or anatomic location on a first attempt is very important.

Even during the biopsy process currently practiced, multiple tissue samples or cores may be taken through the smallest gauge needle possible in an effort to increase biopsy efficacy while decreasing the likelihood of, for example, pneumothorax. However, each time the needle is reinserted, the chances for pneumothorax or bleeding increase. Additionally, due to the small size of the multiple samples, the pathologist may not have the benefit of a sample size large enough to improve the accuracy of diagnosis.

Thus, there exists a need for devices and methods that provide minimally invasive access to a target site or anatomic location, such as lung tissue, for diagnostics and treatment which are able to access the target site more accurately. In the context of the lung, there is a need for such a device that does not increase the risk of causing the lung to collapse, or air or blood entering the pleural space. The present invention satisfies these needs and provides related advantages as well.

SUMMARY OF THE INVENTION

A variety of steerable needles, lancets, trocars, stylets, cannulas, devices and systems are provided for examining, diagnosing, treating, or removing tissue, cells or fluid. The steerable needles, lancets, trocars, stylets, cannulas, devices and systems also provide a platform for delivery of target materials, such as therapeutics, biologics, polymers, glues, etc., to a target site within a patient.

An embodiment of the invention includes a steerable device for use in accessing a target site in a patient comprising: a steerable member adapted to penetrate tissue; and a steering mechanism adapted to be operated by a user to apply a bending force to bend the steerable member to access the target site.

Another embodiment of the invention includes a steerable device for use in accessing a target site in a patient comprising: a steerable member adapted to penetrate tissue; and a steering mechanism adapted to be operated by a user to actively change a shape of the steering member to access the target site.

Still another embodiment of the invention includes a steerable device for use in accessing a target site in a patient comprising: a steerable member adapted to penetrate tissue, the steerable member having a substantially straight shape when in an unstressed condition; and a steering mechanism adapted to be operated by a user to bend the steerable member to access the target site.

In any of these embodiments of the invention, the steering mechanism can be adapted to apply a bending force to the steerable member after penetrating the tissue. Additionally, mechanisms can also be provided that are adapted to apply a bending force that increases the strain on the steerable member to induce curvature. Moreover, the steerable member can be further adapted in the embodiments to create a path to the target site during operation. The steerable device can be adapted to penetrate tissue directly or indirectly, i.e., by being positioned within a device that is adapted to penetrate tissue.

In still other embodiments, an outer sheath can be provided. For the embodiments having an outer sheath, relative positions of a distal end of the steerable member and a distal end of the outer sheath can be adapted to remain the same, or substantially the same, upon application of the bending force.

In yet other embodiments, the steerable device can have a steering mechanism with at least one pull wire, or a plurality of differential wires or pull wires. For other embodiments, the steerable member can be configured to comprise coaxial members. For embodiments with a coaxial member, the coaxial members can comprise an outer needle and a lancet device disposed within the needle and adapted to be bent by the steering mechanism. Thus, for example, the coaxial members can be configured to comprise a lancet device in a first configuration and an aspiration device in a second configuration. Other combinations and configurations are also possible. The device can also be used to guide another instrument to the target site.

Still another embodiment of the invention includes a steerable device for use in accessing target site or anatomic location in a patient comprising: an outer sheath; a steerable member positioned within the outer sheath having a deformable control wire adapted to engage a first end of the steerable member and a second end of the steerable member; and a control mechanism adapted to provide control of a distal end of the steerable device from a proximal end adapted to provide access to a target location of a subject through an access lumen in the patient.

Another embodiment of the invention includes a steerable device for use in accessing target site or anatomic location in a patient comprising: an outer sheath having a flange with an optional position indicator marked on the flange; a steerable member positioned within the outer sheath; and a control mechanism having at least one position indicator on a proximal surface of the control mechanism and which is adapted to provide control of a distal end of the steerable device from a proximal end adapted to provide access to a target location of a subject through an access lumen in the patient.

Yet another embodiment of the invention includes a steerable device for use in accessing a target site or anatomic location in a patient comprising: an outer sheath; a steerable member positioned within the outer sheath having a plurality of control wires adapted to engage a first end of the steerable member and a second end of the steerable member; and a control mechanism adapted to provide control of a distal end of the steerable device from a proximal end adapted to provide access to a target location of a subject through an access lumen in the patient.

Still another embodiment of the invention includes a steerable percutaneous device for use in accessing target site in a patient comprising: an outer sheath; a steerable member positioned within the outer sheath having a steering wire housed within a notched control member; and a control mechanism adapted to provide control of a distal end of the steerable system from a proximal end adapted to provide access to target site of a subject through an access hole in the patient. Access can be made percutaneously, if desired, or by other mechanisms as discussed herein.

Any of the embodiments can also include an outer sheath that is formed of a flexible material. Additionally, embodiments can provide for an outer sheath with a flange at a proximal end. The flange can further be provided with position indicators. In still other embodiments of the invention, the outer sheath can form a cup at a proximal end for engaging a spring, or axial control mechanism, used to control movement of the steerable member in at least one axis.

Embodiments of the device also contemplate use of an external control device that is accessible from a remote location either wired or wirelessly. Such a control mechanism can be configured to engage the steerable member, the outer sheath, the control mechanism, or combinations thereof. Remote access can be from another room, another location, or a position within the room where the patient is not in physical contact with the interventionalist controlling the device.

The control mechanisms of each of the embodiments described enable movement of a distal end of the steerable percutaneous device up to 360° about a first axis, and/or up to 180°, or more, about a second axis.

Embodiments of the invention include appropriate control mechanisms, such as handles, knobs, thumb screws, thumb wires, ball controls and/or joysticks.

The steerable devices can be cannulated. The steerable devices can also be adapted to remove target tissue, cells or fluid, deliver therapy to a target site (including tissues, cells or fluid) or diagnose a target site. In some embodiments, it may be desirable to adapt and configure the steerable member to make it removable from the lumen of the outer sheath, such as once the device has been advanced to the target site. Once removed, the steerable member can be replaced with a member adapted to remove target site, deliver therapy to target site or diagnose target site.

Yet another aspect of the invention provides a biopsy needle whose sampling tip can be more easily steered from outside the patient. Still another aspect of the invention provides a biopsy needle whose sampling tip can be steered and controlled from a position remote from an imaging radiation field. Another aspect of the invention is a steerable biopsy needle whose position can be held in place during imaging. The biopsy needles are adapted and configured to remove tissue, cells or fluids from the target site.

Another aspect of the invention is a steerable needle, lancet, trocar, stylet, cannula, device and/or system that can be easily steered from outside the patient to: a) guide a needle towards an intended target site or target sample; b) guide devices that provide or extract energy to kill or remove cancer cells; and c) guide ports to extract or infuse fluids, solids or glues in or out of body cavities that require assistance to access. The steerable needle, lancet, trocar, stylet, cannula, device and/or system may be removable or integral with any of these devices to simplify use and allow the user to steer at any time during the procedure. Devices that incorporate aspects of the steerable aspect of the invention include, for example:

a. Co-axial dual members: wherein an outer needle is guided by a steerable needle, lancet, trocar, stylet, cannula, device and/or system and the device can be replaced by a second inner device that is used to aspirate a target tissue, such as cancer cells, for biopsy and diagnostic characterization. The outer needle can be left in place to be used as a guide for the inner needle to harvest multiple sequential samples.

b. Steerable needle, lancet, trocar, stylet, cannula, device and/or system that can steer a flexible cannula to regions in a patient's body that cannot otherwise be accessed or present anatomical challenges in accessing. The steerable needle, lancet, trocar, stylet, cannula, device and/or system may be removed to increase the port lumen size to enhance drainage or infusion of liquids, solids or materials that solidify such as glues.

c. A steerable needle, lancet, trocar, stylet, cannula, device and/or system comprised of or made to guide a tissue removing device. Such an embodiment would include a device that may use stored energy to shear tissue in order to sample and examine its condition. The device can be used to sample or extract cancerous tissue or entire tumors. The device may also use radio frequency waves to simultaneously cut tissue and coagulate blood that could otherwise cause bleeding complications.

d. A steerable needle, lancet, trocar, stylet, cannula, device and/or system may be devised to extract heat energy in order to freeze and kill pathologic tissue.

e. A steerable needle, lancet, trocar, stylet, cannula, device and/or system may be devised to deliver energy in order to heat and kill pathologic tissue. The energy can be delivered to the tissue in the form of light or magnetic energy such as radio frequency, microwave, ultrasound, laser derived light, or radiation wave forms such as x-ray energy. A device that delivers any combination of cryoablation and the other forms of energy can be configured to kill tissue with different levels of intensity and depth. This adaptability is useful for widespread dense tumors. The steering feature allows for convenient and quick use of the different energy modalities to be applied to different regions within the patient.

In an embodiment of the methods of the invention, a method is provided for delivering a device to a target site in a patient comprising: penetrating tissue with a steerable member; and applying a bending force after penetrating the tissue to bend the steerable member to deliver the device to the target site.

In another embodiment of the methods of the invention, a method is provided for delivering a device to a target site in a patient comprising: penetrating tissue with a steerable member; and actively changing a shape of the steering member after penetrating the tissue to deliver the device to the target site.

In still another embodiment of the methods of the invention, a method is provided for delivering a device to a target site in a patient comprising: introducing a steerable member through a scope; and applying a bending force to bend the steerable member to deliver the device to the target site.

In some embodiments of these methods the further step of advancing the steerable member through the tissue is provided. In other embodiments, the method of applying a bending force further comprises bending a bendable portion of the steering member while the bendable portion of the steering member is positioned within tissue. In some embodiments of the method, the further step of aspirating at the target site can be provided. In still other embodiments of the method, the further step of removing target material (e.g., tissue, cells or fluid) at the target site, draining the target site, infusing the target site with a marking, therapeutic or diagnostic material, delivering energy to the target site, extracting heat energy from the target site, and/or killing target material at the target site can be included.

Embodiments of the invention also include a method of using a steerable device having an outer sheath and a steerable member, comprising: introducing a steerable device; advancing the device toward a target site; and deforming a distal tip of device from a longitudinal axis of a device. In some methods the step of applying a force to the distal tip of the device is accomplished remotely. Applying a force includes bending or deforming the distal tip. In at least some embodiments, the bending caused by the application of force can be up to 360° around a first axis, and/or up to 180°, or more, around a second axis. In some methods, the embodiments include the additional step of removing the steerable member and replacing the member with a member adapted to remove target tissue, cells or fluid, deliver therapy to target tissue, cells or fluid, or diagnose target tissue, cells or fluid.

Another aspect of the invention includes a method comprising the steps of: determining, using diagnostic testing, that a steerable device must be advanced to a specific location in the body; introducing the device into the body; and manipulating the shape of the device to cause shape changes while the device is in the body to influence a new path of advancement for the device. The method can be achieved by a device enabling remote access and control of the steerable devices disclosed.

Yet another aspect of the invention includes a method comprising the steps of: determining, using diagnostic testing devices, that a device must be advanced to a specific location in the body; introducing a steering device into the body; manipulating the shape of the steering device to cause shape changes while it is in the body to influence a new path of advancement; and introducing an instrument into the body.

Still another aspect of the invention includes a method comprising the steps of: determining, using diagnostic testing devices, that foreign matter exists in a patient's body that must be sampled; introducing a sampling instrument into the body; and manipulating the shape of the instrument to cause shape changes while the instrument is in the body to influence a new path of advancement.

Still another aspect of the invention includes a method comprising the steps of: using a device to obtain an image of a patient's body along with the steerable device contained therein. The image can be obtained at discrete intervals or concurrently to advancing and steering the device using techniques available in the art.

Yet another aspect of the invention includes a method comprising the steps of determining, using a diagnostic testing device, that foreign matter exists in a patient's body that must be sampled; introducing a steering element into the body; manipulating the shape of the element to cause shape changes while it is in the body to influence a new path of advancement; introducing a sampling instrument into the body; and imaging the body and device.

Still another aspect of the invention includes a method comprising the steps of: determining, using a diagnostic testing device, that foreign matter exists in a patient's body that must be sampled; introducing a steering element into the body; manipulating the shape of the instrument to cause shape changes while the instrument is in the body to influence a new path of advancement; imaging the body and device.

Another aspect of the invention includes a method comprising the steps of: determining, using a diagnostic testing device, that foreign matter exists in a patient's body that must be sampled; introducing a needle instrument into the body that can be steered; manipulating the shape of the instrument to cause shape changes while the instrument is in the body to influence a new path of advancement; imaging the body and device.

Still another aspect of the invention includes a method comprising the steps of: determining, using a diagnostic testing device, that foreign matter exists in a patient's body that must be sampled; introducing a sampling instrument into the body; manipulating the shape of the instrument to cause shape changes while the instrument is in the body to influence a new path of advancement from a location more than 2 inches away from the body entry point; and imaging the body and device.

Another aspect of the invention includes a method comprising the steps of: determining, using a diagnostic testing device, that foreign matter exists in a patient's body that must be sampled; introducing a steering element into the body; manipulating the shape of the element to cause shape changes while the instrument is in the body to influence a new path of advancement from a location more than 2 inches away from the body entry point; imaging the body and device.

Yet another aspect of the invention includes a method comprising the steps of: determining, using a diagnostic testing device, that foreign matter exists in a patient's body that must be sampled; introducing a steering element into the body; manipulating the shape of the steering element to cause shape changes while the instrument is in the body to influence a new path of advancement from a location more than 2 inches away from the body entry point; imaging the body and device using an imaging device; and introducing a sampling instrument into the body.

Still another aspect of the invention includes a method for palpating, encapsulating, isolating, removing and killing target tissue, cells or fluid in a patient's body by advancing a steerable device to the target site.

Another aspect of the invention includes the provision of devices and materials disclosed in the form of a kit.

INCORPORATION BY REFERENCE

All publications and patent applications mentioned in this specification are incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1A:
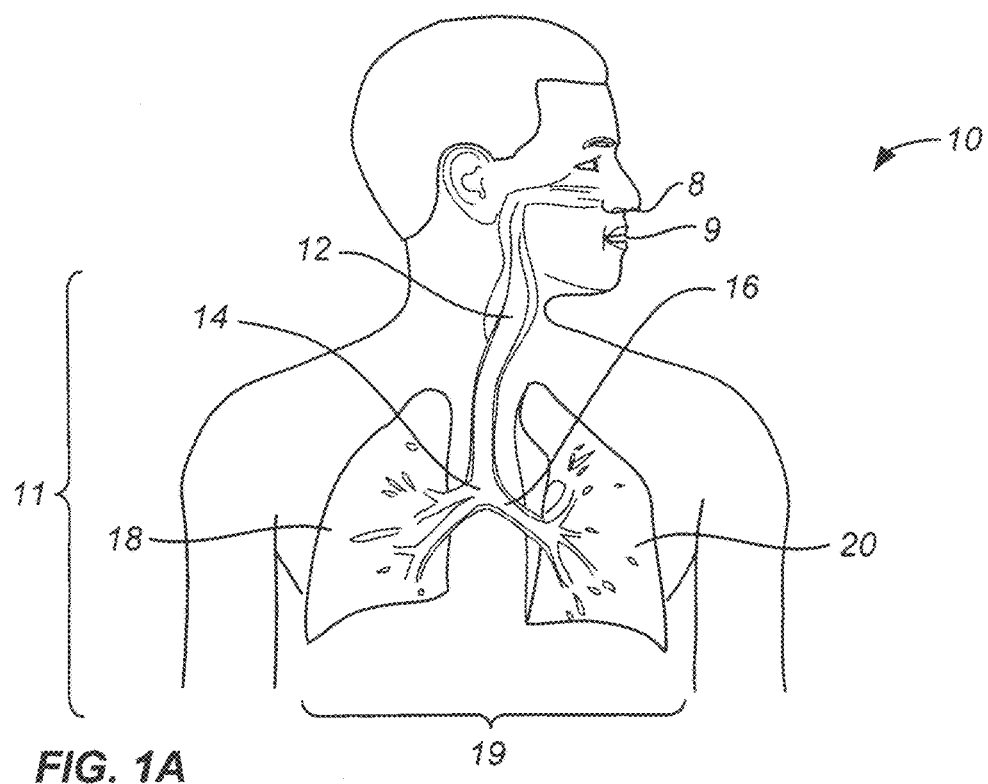
FIGS. 1A-D illustrates the anatomy of the respiratory system, along with an example of hemothorax caused from blood entering the pleural space.

As noted above, the present invention is suitable for use in percutaneously accessing a target site within a body, as well as traversing tissue and lumens between an access point on the body and a target site in the body. The invention is also suitable for accessing a target site through body lumens such as the trachea and the vasculature. A target site can be located in any anatomic location in the body. Typically a site is identified by the physician or radiologist and the tissue, cells and/or fluid, or other material at that site, is then identified as target material and selected or targeted for access. Thus, for example, the target tissue, cells or fluid can be the target material identified for access from: brain, heart, liver, kidney, thyroid, lung, pancreas, intestine, uterine, ovary, prostate, lymph, spleen, skin, biliary, parathyroid, pituitary, adrenal gland, mediastinum, bladder, connective tissue, breast, gastrointestinal tract, joints, muscle, etc. Additionally, in some instances it is desirable to access a target site located within a void, such as a space between organs, lumen, etc. In that instance, the target site may include fluid, or other material which is the target for access. Once the target site is accessed and target material (e.g. tissue, cells and/or fluid) is identified for access, one or more diagnostic, therapeutic or delivery procedures can be employed to remove, treat and/or mark the target material.

An application of the device includes safely performing a transthoracic procedure without impacting the negative pressure required to maintain lung function. Thus, in addition to other applications, the present devices allow accessing the interior of the lung or the surrounding tissue to perform therapeutic or diagnostic functions while reducing the risk of complications associated with the accessing procedure. The present invention includes the use of the disclosed devices with, for example, a bronchoscope. See, for example, U.S. patent application Ser. No. 11/153,296 filed Jun. 18, 2005 entitled Lung Access Device (Mathis). The devices disclosed can also be adapted for use with other devices, without departing from the scope of the invention.

The invention provides methods, and devices for obtaining target material from a body, such as lung tissue. Although the device can be used to obtain a variety of target materials, such as tissue, within a body, for purposes of illustration the device arid its operation will be discussed in the context of lung tissue, which presents additional challenges for biopsy capture also addressed by the designs of the invention. Additionally, the devices can be used in combination with suitable rigid, flexible, and steerable scopes, such as a bronchoscope. Other scopes, including, but not limited to, colonoscopes, thoracoscopes, laparoscopes, and/or endoscopes, can also be used, depending upon the location of the target site to be accessed. Additional information pertaining to scopes is available in; for example, U.S. Pat. No. 6,478,730 entitled Zoom Laparoscope (Bala et al.); U.S. Pat. No. 6,387,044 entitled Laparascope Apparatus (Tachibana et al.); U.S. Pat. No. 6,494,897 entitled Method and System for Performing Thoracoscopic Cardiac Bypass Surgery (Sterman et al.); U.S. Pat. No. 6,964,662 entitled Endoscopic Forceps Instrument (Kidooka); 6,967,673 entitled Electronic Endoscope System with Color-Balance Alteration Process (Ozawa et al.).

The invention also provides methods for encapsulating target material, killing target material, including muscle, nerve, connective and epidermal tissue and interstitial fluids, providing a mechanism for palpating a target site, and delivering target markers and biologically active and/or therapeutic compounds to a target site.

As mentioned, the lung is used to illustrate the advantages and operation of the devices disclosed. FIG. 1A illustrates the respiratory system 10 located primarily within a thoracic cavity 11. The respiratory system 10 includes the trachea 12, which brings air from the nose 8 or mouth 9 into the right primary bronchus 14 and the left primary bronchus 16. From the right primary bronchus 14 the air enters the right lung 18; from the left primary bronchus 16 the air enters the left lung 20. The right lung 18 and the left lung 20, together comprise the lungs 19. The left lung 20 is comprised of only two lobes while the right lung 18 is comprised of three lobes, in part to provide space for the heart typically located in the left side of the thoracic cavity 11, also referred to as the chest cavity.

Figure 1B:
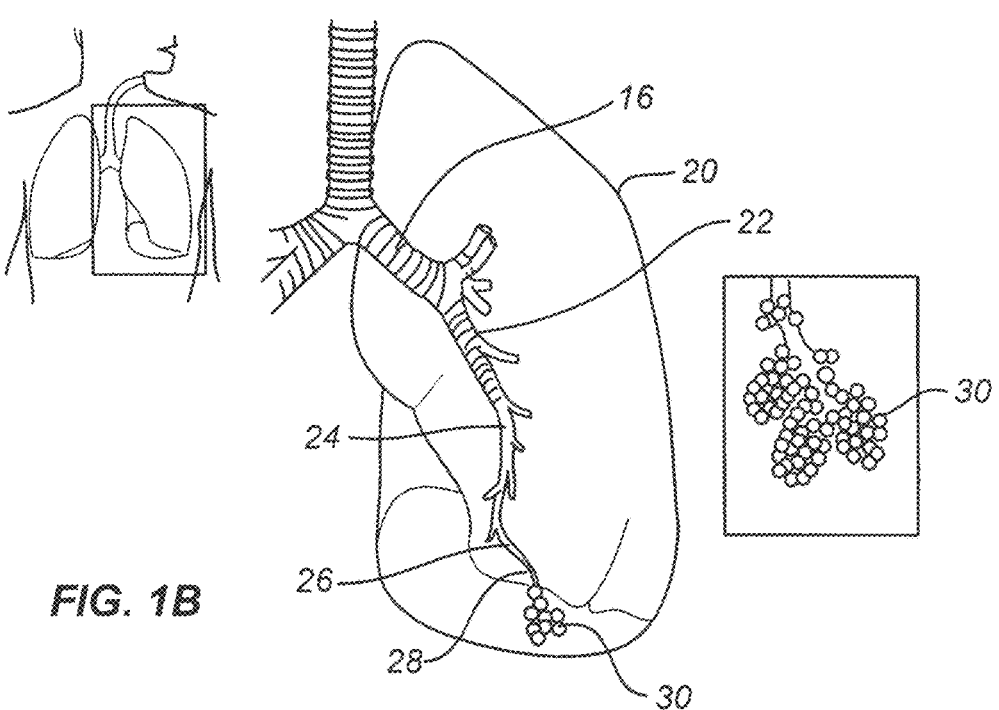
Figure 1C:
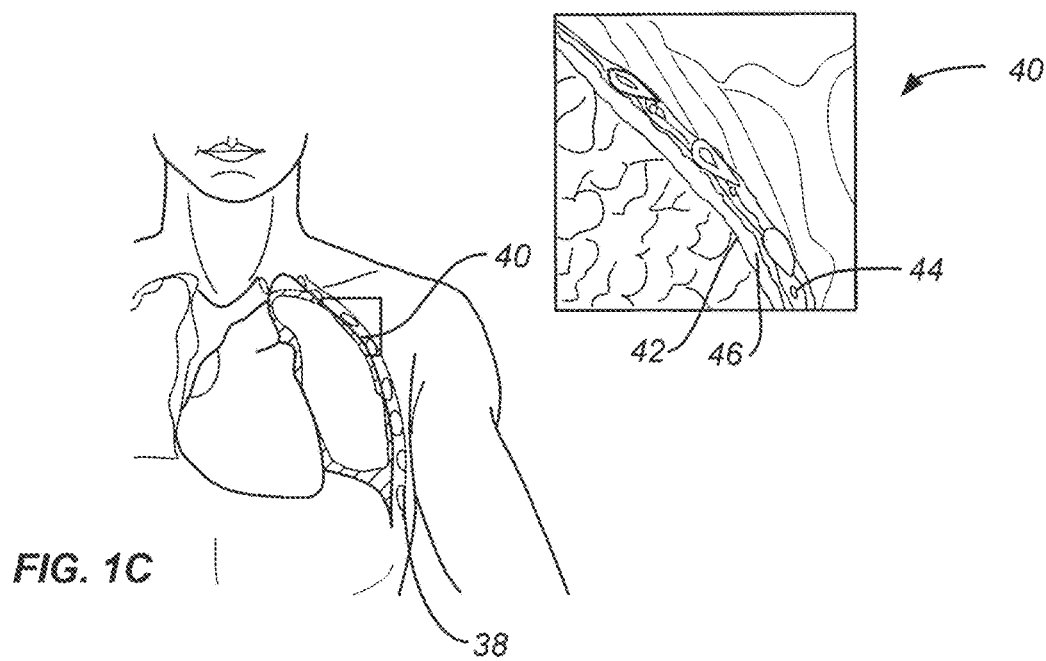

As shown in more detail in FIG. 1B, the primary bronchus, e.g. left primary bronchus 16, that leads into the lung, e.g. left lung 20, branches into secondary bronchus 22, and then further into tertiary bronchus 24, and still further into bronchioles 26, the terminal bronchiole 28 and finally the alveoli 30. The pleural cavity 38 is the space between the lungs and the chest wall. The pleural cavity 38 protects the lungs 18, 20 and allows the lungs to move during breathing. As shown in FIG. 1C, the pleura 40 defines the pleural cavity 38 and consists of two layers, the visceral pleurae 42 and the parietal pleurae 44, with a thin layer of pleural fluid therebetween. The space occupied by the pleural fluid is referred to as the pleural space 46. Each of the two pleural layers 42, 44 are comprised of very porous mesenchymal serous membranes through which small amounts of interstitial fluid transude continually into the pleural space 46. The total amount of fluid in the pleural space 46 is typically slight. Under normal conditions, excess fluid is typically pumped out of the pleural space 46 by the lymphatic vessels.

The lungs 19 are an elastic structure that float within the thoracic cavity 11. The thin layer of pleural fluid that surrounds the lungs 19 lubricates the movement of the lungs within the thoracic cavity 11. Suction of excess fluid from the pleural space 46 into the lymphatic channels maintains a slight suction between the visceral pleural surface of the lung pleura 42 and the parietal pleural surface of the thoracic cavity 44. This slight suction creates a negative pressure that keeps the lungs 19 inflated and floating within the thoracic cavity 11. Without the negative pressure, the lungs 19 collapse like a balloon and expel air through the trachea 12. Thus, the natural process of breathing out is almost entirely passive because of the elastic recoil of the lungs 19 and chest cage structures. As a result of this physiological arrangement, when the pleura 42, 44 is breached, the negative pressure that keeps the lungs 19 in a suspended condition disappears and the lungs 19 collapse from the elastic recoil effect.

When fully expanded, the lungs 19 completely fill the pleural cavity 38 and the parietal pleurae 44 and visceral pleurae 42 come into contact. During the process of expansion and contraction with the inhaling and exhaling of air, the lungs 19 slide back and forth within the pleural cavity 38. The movement within the pleural cavity 38 is facilitated by the thin layer of mucoid fluid that lies in the pleural space 46 between the parietal pleurae 44 and visceral pleurae 42.

Figure 1D:
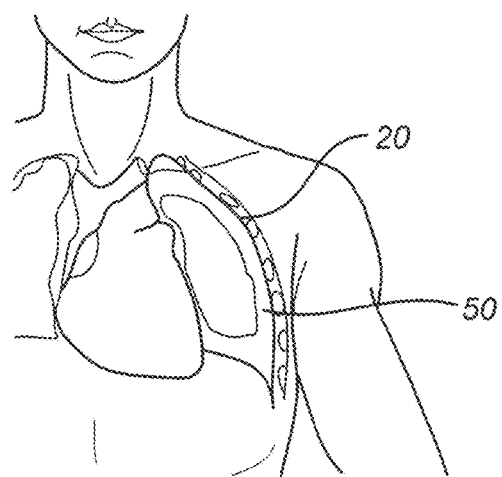

For purposes of illustration, FIG. 1D illustrates a lung 20 with blood 50 in the pleural space (also referred to as hemothorax). As evidenced from the drawing, the presence of blood 50 in the pleural space 46 results in a contraction of the lung 20 to a much smaller size. Clinically, the patient would have a difficult time breathing air into the collapsed lung because the act of breathing relies on the lungs being suspended in a state of negative pressure. As will be appreciated by those of skill in the art, fluid or air within the pleural space 46 will achieve a similar clinical impact on the size of the lung relative to the thoracic cavity as the hemothorax illustrated in FIG. 1D. Because of the anatomical design of the lungs, and the negative pressure required to maintain the lungs in a suspended state, obtaining tissue samples from the lungs presents additional challenges that are not present for other tissues.

Figure 2A:
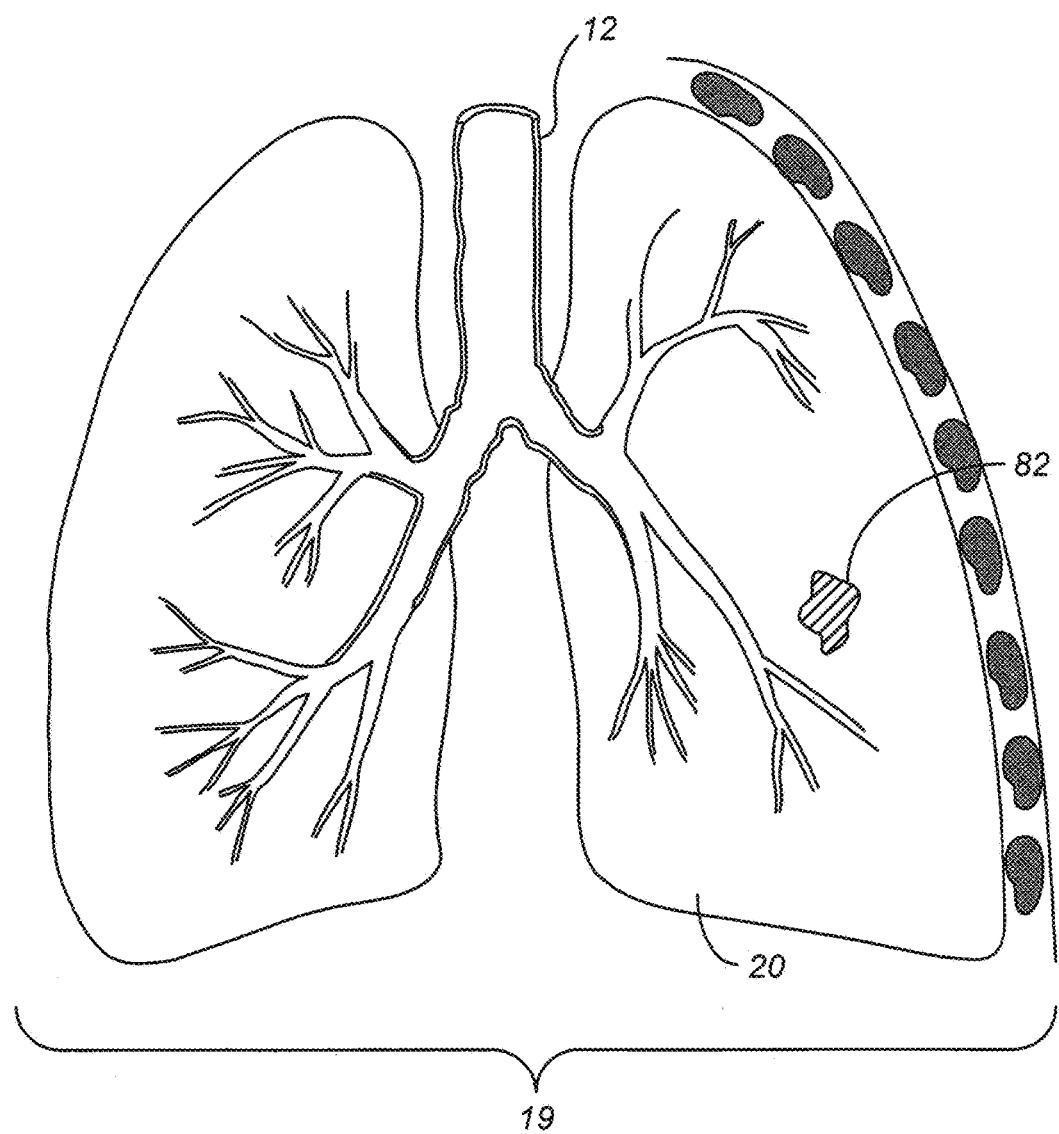
FIG. 2A illustrates a lung having a target site for biopsy.
Figure 2B:
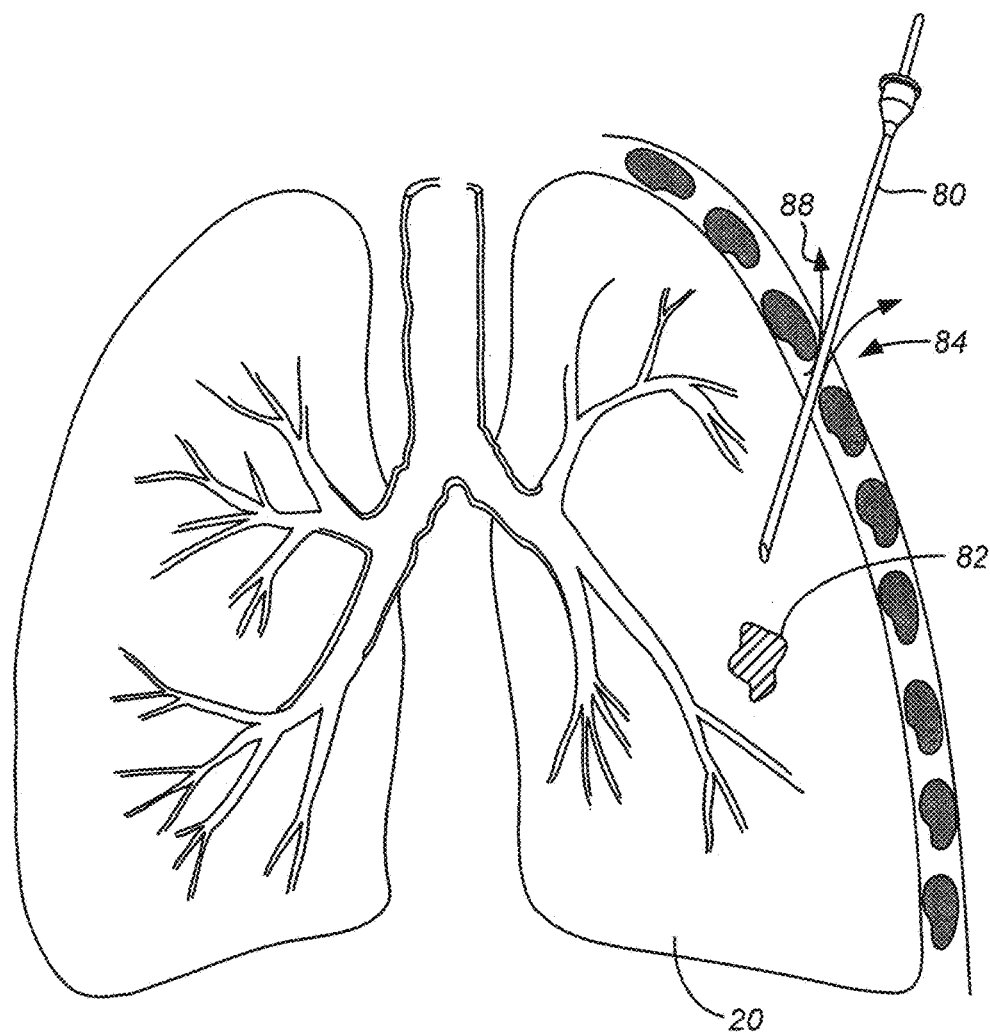
FIG. 2B illustrates a needle being advanced toward the target site.
Figure 2C:
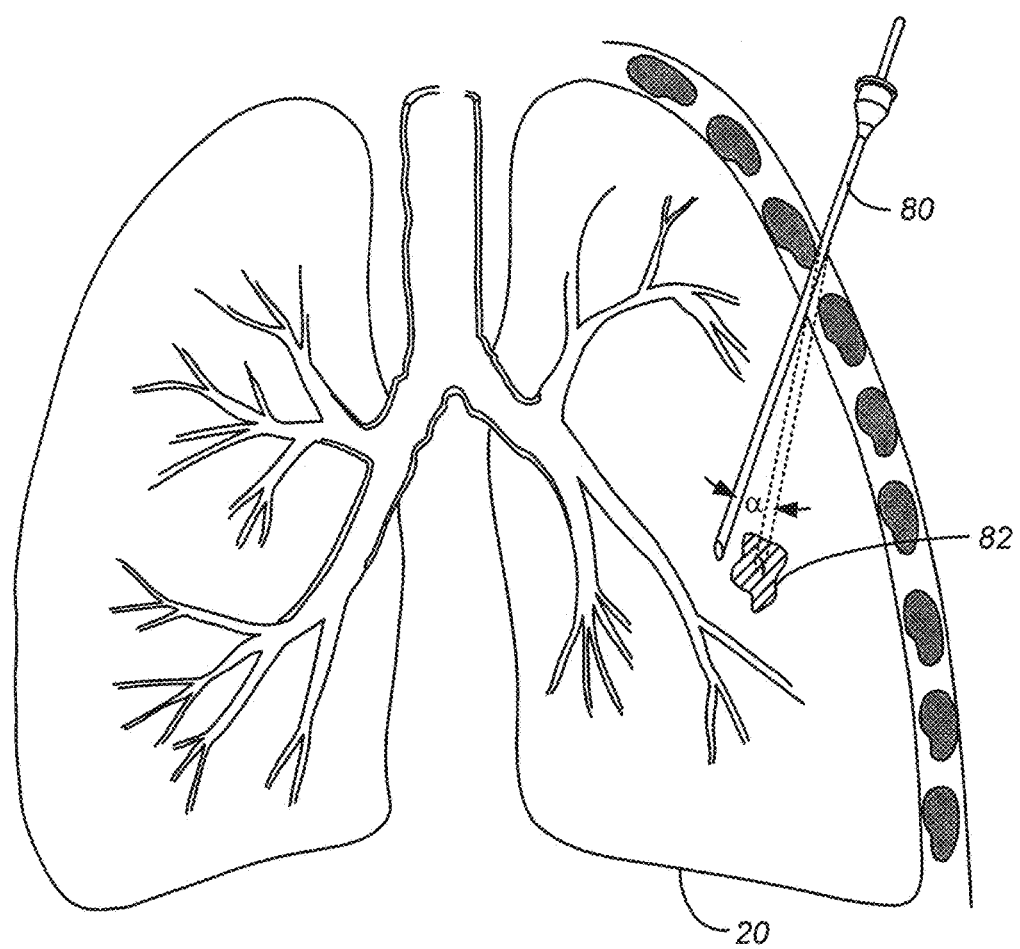
FIG. 2C illustrates a needle that has been advanced toward the target site but which has failed to connect to the tissue.

FIGS. 2A-C depict the lungs 19 during a procedure wherein a biopsy device 80 is deployed to obtain a target sample 82, or target material, from the lung and breaches the pleura. As a result of the breach, air 88 inside the affected lung 20 exits the lung (indicated by arrows) around the opening 84 in the lining made by the device 80. As in the previous example, air inside the affected lung 20 exits the lung (indicated by arrows) around the opening 84 created when the device 80 punctured the wall of the bronchus 14. Additionally, as will be appreciated by those of skill in the art, the trajectory of the device 80 can be such that the device 80 fails to access the target site for a biopsy, as illustrated in FIG. 2C.

As stated above, the invention and its embodiments are described for purposes of illustration with respect to access, diagnostic treatment and removal of target tissue, cells or fluid in the lung. However, aspects of the devices and methods are applicable to diagnostic and therapeutic procedures for other target tissues, cells or fluids within the body as well.

Figure 3:
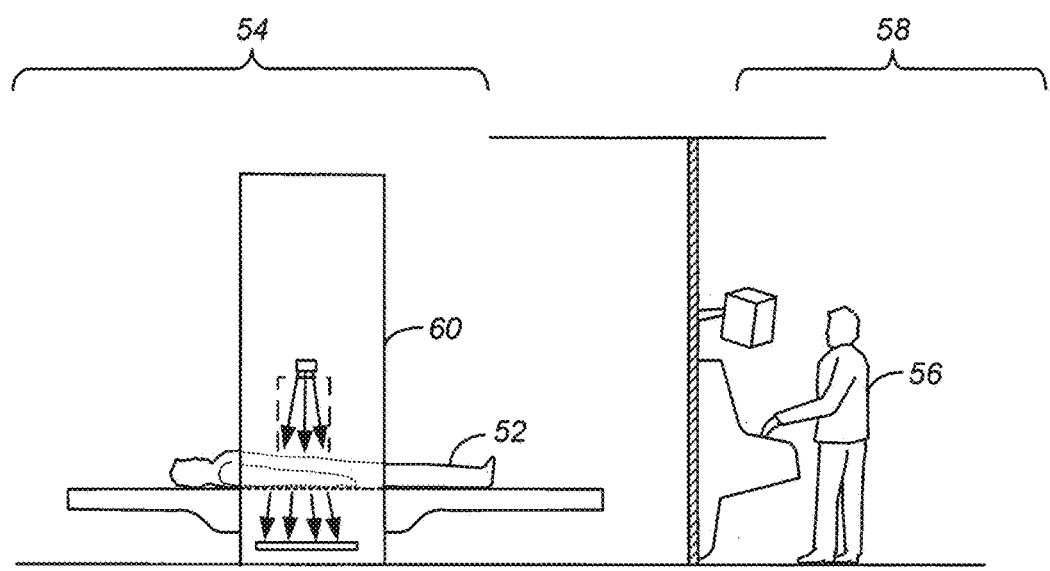
FIG. 3 illustrates a patient in an image capture chamber with a technician monitoring the process from another room.

FIG. 3 illustrates a patient 52 in an image capture chamber 54, such as a room having an x-ray machine, with a physician or technician 56 monitoring an image capture process from, for example, a location 58 such as a separate room. The image capture process employs a machine 60 suitable for image capture. Often when patients 52 undergo a procedure to obtain a target sample, an attempt is made to position a device to access a target site and then a confirmatory image is taken to ensure that the target material was obtained. As will be appreciated by those of skill in the art, suitable mechanisms for determining the location of the device used to access a target material relative to the target site employs, unless otherwise indicated, conventional devices 60 and methods and techniques known in the art. These conventional devices and techniques include: x-ray imaging and processing, x-ray tomosynthesis, ultrasound including A-scan, B-scan and C-scan, computed tomography (CT scan), spiral CT, magnetic resonance imaging (MRI), optical coherence tomography, single photon emission computed tomography (SPECT) and positron emission tomography (PET), fluoroscopy and combinations and portable versions thereof are within the skill of the art. Such techniques are explained fully in the literature and need not be described herein. See, e.g., X-Ray Structure Determination: A Practical Guide, 2nd Edition, editors Stout and Jensen, 1989, John Wiley & Sons, publisher; Body CT: A Practical Approach, editor Slone, 1999, McGraw-Hill publisher; X-ray Diagnosis: A Physician's Approach, editor Lam, 1998 Springer-Verlag, publisher.

FIGS. 4A-E illustrate perspective and cross-sectional views of a steerable device 100 capable of accessing a target sample of material from a target site. Components of the device 100 include an optional outer sheath 110, which can be in the form of a cannula, flexible tube or hypotube, to name a few, and a steerable member 120. The sheath can be made from suitable biocompatible polymers and metals such as titanium and nickel-titanium alloys (Nitinol), stainless steel, fluoropolymers, polyetheretherketone (PEEK), polytetrafluoroethylene (PTFE), expanded polytetrafluoroethylene (ePTFE), polyurethane, nylons, polyimide films (Kapton®), and the like. Reference to suitable polymers that can be used in the invention can be made found in: PCT Publication WO 02/02158 A1, dated Jan. 10, 2002, entitled Bio-Compatible Polymeric Materials; PCT Publication WO 02/00275 A1, dated Jan. 3, 2002, entitled Bio-Compatible Polymeric Materials; and, PCT Publication WO 02/00270 A1, dated Jan. 3, 2002, entitled Bio-Compatible Polymeric Materials.

A control mechanism 130 adapted to be controlled by a user, such as a technician, is provided at a proximal end 102 to enable steering. The distal end 104, which is positioned away from the proximal end typically positioned outside the patient's body (or nearest a user), can be adapted and configured in a variety of ways to achieve the diagnostic or therapeutic objective of the device. For example, the distal end 104 can be configured as a trocar, lancet, stylet, needle, therapeutic delivery device, marker, or diagnostic delivery device, to name a few. In the embodiment depicted, the control mechanism 130 at the proximal end 102 includes a knob 132 and a spring 134 or coil. Proximal and distal are, however, relative terms, which do not limit the scope of the description.

The spring 134 may be a coiled wire formed of suitable material capable of maintaining a desired spring tension. A plurality of coils of the coiled body form a lumen sized and adapted to fit around the exterior of the control mechanism 130. Some embodiments include a second coiled body along with a first coiled body. As illustrated in the cross-sectional longitudinal views of FIGS. 4B and 4C, the steerable member 120 is located within the outer sheath 110 such that the steerable member 120 is capable of longitudinal movement 106 within a lumen 112 in the sheath 110. The spring 134 at the proximal end 102 fits within an section of the sheath 110 that has a lumen 112' at its proximal end 102 having a diameter large enough to accommodate the steerable member 120 and the spring 134. Thus, the sheath cups the spring at its proximal end. Although the spring 134 can be formed from, for example, a compression sleeve, it is anticipated that typically a spring 134 is provided that is formed from a material capable of forming a spring with optimal spring force, such as stainless steel. However any structure capable of providing spring force to the device for controlling the movement of the steerable member 120, as discussed herein, will be suitable, as will be appreciated by those of skill in the art.

In addition to the longitudinal movement along a longitudinal axis L that is achievable by pulling and pushing the knob 132 proximally and distally, rotational movement 108 is also achievable by turning the knob 132 clockwise and counterclockwise, as desired. Thus, the distal end of the steerable device is capable of 360° movement about at least one axis.

Figure 4A:
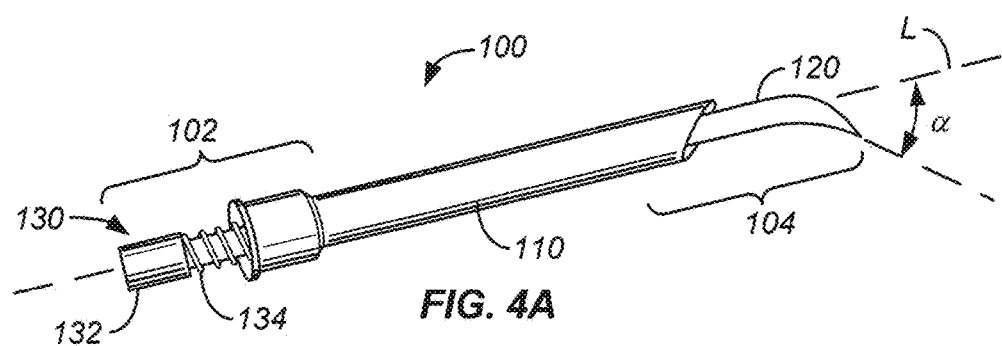
FIGS. 4A-E illustrate perspective and cross-sectional views of a steerable device capable of accessing target site or anatomic locations.
Figure 4B:
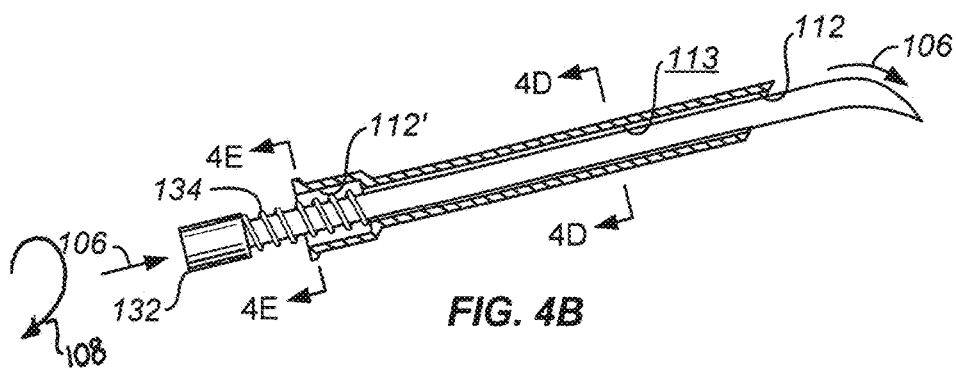
Figure 4C:
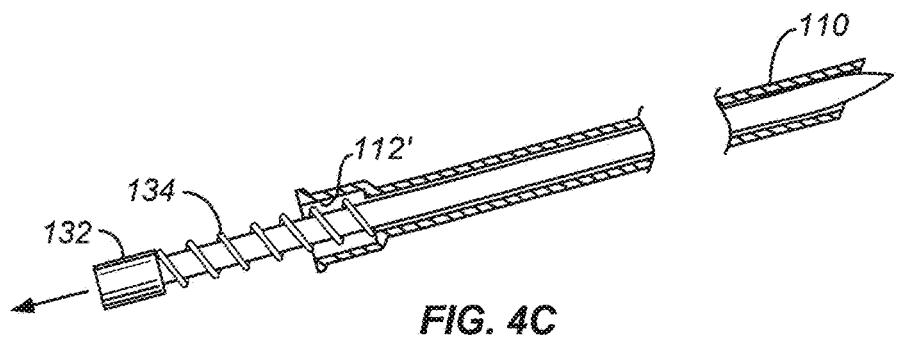
Figure 4D:
Figure 4E:
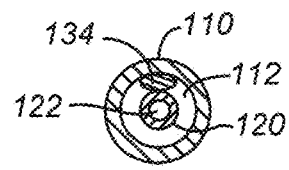

From the cross-sectional view shown in FIG. 4D, which is taken along the lines D-D in FIG. 4B and perpendicular to the longitudinal axis L of the device 100, the outer sheath 110 has a lumen 112 sized to receive a steerable member 120 such that the steerable member 120 can move within the lumen 112 of the outer sheath 110. As illustrated in the cross-sectional view of FIG. 4E, taken along the lines of E-E of FIG. 4B, the diameter of the outer sheath 110 is larger relative to the diameter of the steerable member 120 such that at least a portion of spring 134 can be positioned between the two components. Thus, the steerable member 120 has been illustrated with a central lumen 122. Such a configuration would be useful where the steerable member 120 is adapted, for example, to deliver therapy (e.g. materials to a target site), or remove target tissue, cells or fluid, to name a few. The proximal end of the outer sheath 120 has a larger diameter and forms a cup for retaining or engaging at least a portion of the spring. The steerable member 120 can be formed of any suitable material including shape memory nickel-titanium alloys (Nitinol); the outer sheath can be formed from any suitable material such as stainless steel, titanium tubing or biocompatible polymers. The steerable member 120 can be configured to lock or engage the outer sheath 110 to control the relative movement of the steerable member 120 to the outer sheath 110.

In at least one embodiment, the device 100 is radiopaque at least at its distal tip. The outer sheath 110 can also be formed from plastic with a metal tip or a polymer that has been loaded with bismuth, tantalum, platinum, or other dense metal. The sheath can also be formed from nickel-titanium super elastic shape memory alloys (Nitinol), including normalized, austenitic or martensitic forms. The outer diameter of the sheath, or exterior profile, can be from 10-28 gauge, more typically around 23 gauge. The overall length of the device 100 can be anywhere from 1 inch to, for example, 17 inches, or any suitable length.

In operation of the steering features, as the steerable member 120 is advanced in a distal direction and exits the distal end 104 of the sheath 110, the distal end of the steerable member 120 assumes a curved shape that deviates away (angle α) from a longitudinal axis L of the device 100. The outer sheath 110 or steerable member 120 can act as a dilator. The amount of deviation away from the central axis L is controlled by the user and the amount of distance the distal end 104 of the steerable member 120 extends out of the sheath 110. As the steerable member 120 is drawn back into the sheath 110 (i.e., pulled proximally toward the user and/or controls), the angle α is decreased. The reduction of angle α a can be caused by pressure applied to the steerable member 120 by the interior surface 113 of the sheath 110 which causes the steerable member 120 to straighten out. Thus, when advancing toward a target site, the entire mechanism (sheath 110 and steerable member 120) is advanced toward the tissue. As the location of the device 100 relative to the target site is assessed (using, for example, an image capture machine 60 discussed with respect to FIG. 3) and it is determined that the trajectory of the device 100 has deviated from the desired target site (see, for example, FIGS. 2B-C), the steerable member 120 can be advanced distally toward the tissue while maintaining the sheath 110 in a fixed, or largely fixed location, to enable the device 100 to reach the target site. As will be appreciated by those of skill in the art, the step of advancing the device 100, and advancing only the steerable member 120 can be alternated as required to optimize accessing the target site. In addition to controlling the location of the device 100 by advancing the device 100 and/or the steerable member 120, further control can be achieved by rotating the knob 132 clockwise and counterclockwise. The position of any or all components of the device can be locked into place, e.g. by engaging the steerable member 120 and the outer sheath 110, to prevent further movement of the device 100 or device components, as desired.

The device 100 can achieve, for example, up to 360° movement about at least one axis, such as longitudinal axis L, and up to 180°, or more, movement about any remaining axes, depending upon the curve of the steerable member. Greater or less steerability can be provided for by altering the design of the device as disclosed herein. Once the device is in place, the steerable member 120 can be withdrawn from the outer sheath 110 and replaced with, for example, a syringe, or other suction source, and a tissue sample may then be aspirated into the outer sheath and withdrawn from the patient. Additionally, the two part configuration enables the outer sheath 110 to be made with a thinner wall which results in an overall lower profile (i.e., diameter or circumference) making the device less invasive. Alternatively; the steerable member 120 can be replaced with a device or system that administers therapy to the target site.

FIGS. 5A-F illustrate perspective and cross-sectional views of another steerable device 200 capable of accessing a target site. The steerable device 200 has a proximal end 202 and a distal end 204. An optional sheath 210 is provided having an inner lumen 212 for receiving a steerable member 220. In the configuration shown in FIG. 5, the steerable member 220 has a notched tubular member 221 that houses an inner control member 223.

The inner control member 223 is configured to have a distal end having a diameter larger than the inner diameter of the notched tubular member 221, such that the distal end extends beyond the distal end of the tubular member and is prevented from being pulled within the lumen of the notched tubular member. Thus the distal end of the inner control member 223 can form an end 224 such as a ball or bulbous end, as depicted, or a flange that catches the notched tubular member. As will be appreciated by those skilled in the art, the distal end of the inner control member 223 can also be removable. In one configuration, the end 224 can be removably attachable to the end of the control member 223 by appropriate mechanisms, e.g. threaded male end on the control member 223 engaging a threaded female end of the end 224. In another configuration, the end 224 can be soldered to the control member 223, if desired. Designs where the end 224 and control member 223 act in a unified manner, including designs where the control member 223 and end 224 are one piece, are also within the contemplated design. The inner control member 223 is capable of movement 206 along a longitudinal axis L of the device 200, as well as rotational movement 208 clockwise and counter-clockwise around the longitudinal axis L of the device 200.

The notched tubular member 221 has an inner lumen 222 that is configured to surround the control member 223 and engage the end 224 at the distal end of the tubular member 221. The notched tubular member 221 can also be adapted and configured to fit within the lumen 212 of the optional sheath 210, as illustrated. When placed within the sheath 210, the notched tubular member 221 has at least a portion that is capable of movement 206 along a longitudinal axis L of the device 200. Additionally, at least a portion of the tubular member 221 is fixed within the sheath 210. In one configuration, the notched tubular member 223 is adapted to fixedly engage the sheath 210 at a proximal end 202. For example, the notched tubular member 223 can be adhered to the sheath 210 at a proximal location, or can be releasably engaged at a proximal location (e.g., by using threads or tongue and groove designs).

Figure 5A:
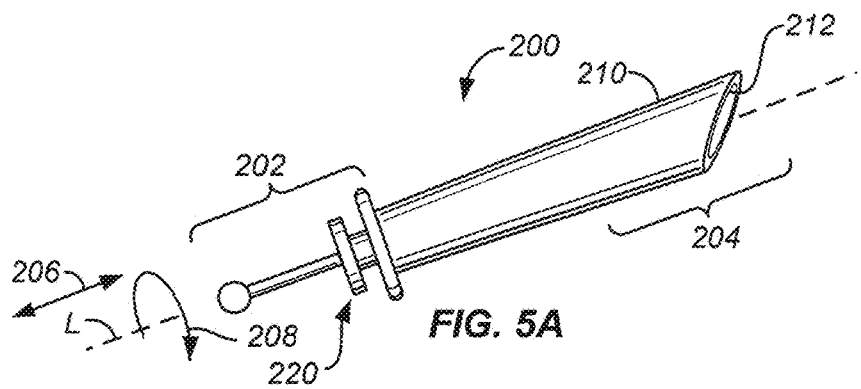
FIGS. 5A-F illustrate perspective and cross-sectional views of another steerable device capable of accessing target site or anatomic locations.
Figure 5B:
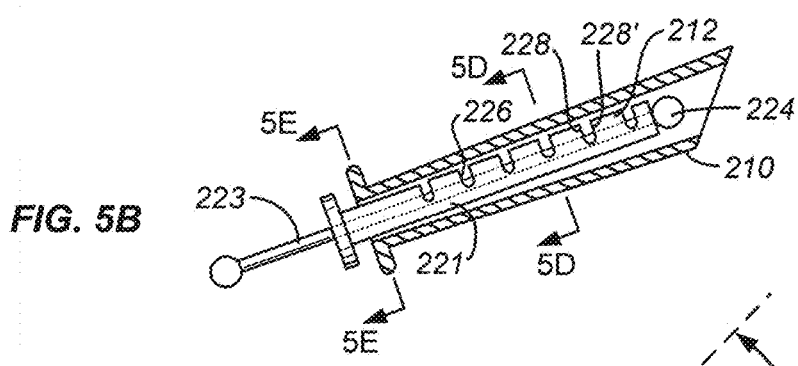
Figure 5C:
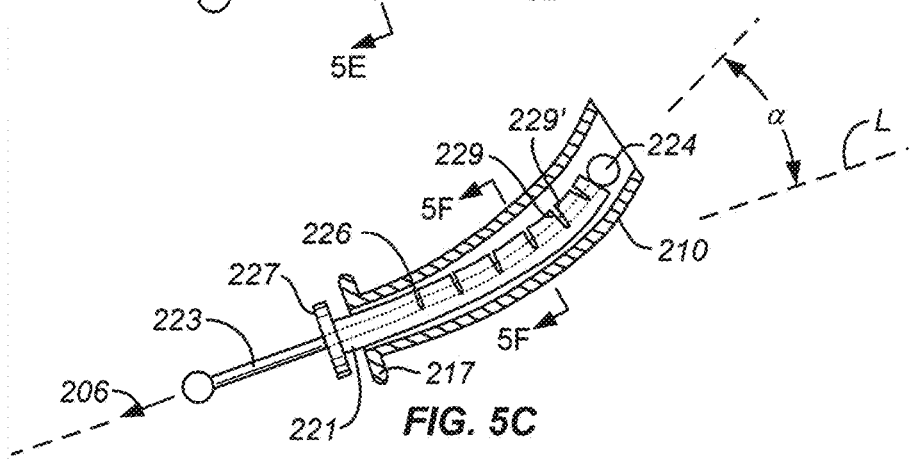
Figure 5D:
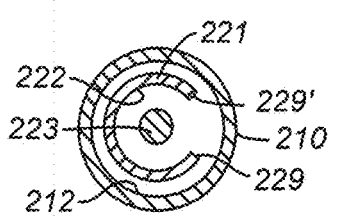
Figure 5E:
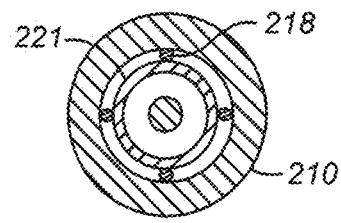

Turning to the cross-sections taken along a plane perpendicular to the longitudinal axis L along the length of the device 200 shown in FIGS. 5D-E, it can be seen that the control member 223 is positioned within a lumen 222 of the notched tubular member 221. Where the notched tubular member 221 cross-section cuts across a notched section of the tubular member 221, the lumen 222 defined by the tubular member 221 at that cross-section communicates with the lumen 212 defined by the sheath 210, as shown in FIG. 5D. Conversely, where the notched tubular member 221 cross-section cuts across a section of the tubular member 221 that is not notched, the lumen 221 defined by the tubular member 221 at that cross-section may not communicate with the lumen 212 defined by the sheath 210. The notches 226 can be configured such that a profile, or side view, along a longitudinal axis of the tubular member 221 form a semi-circular shape, or u shaped (as illustrated in FIG. 5B), a triangular shape, a square shape, etc. Notches 226 can be in the form of cuts or ridges as well. Regardless of the geometric profile of the notch 226 in a dimension, from at least one view, the upper opposing edges 228, 228' of the notch are positioned such that the opposing edges 228, 228' approach each other when the notches are compressed by moving the control member 223. In some configurations, when the upper opposing edges 228, 228' of the notches 226 are compressed at least a portion of the edge 228 of the notch 226 may appear to disappear completely, e.g., where the sides of the notches 229, 229' come into contact with each other and appear to form a seam. However, as well be appreciated by those skilled in the art, other configurations of the tubular member are possible. For example, the cross-section at FIG. 5E can be adapted to engage at a location along its circumference, such as by forming a seam.

Figure 5F:
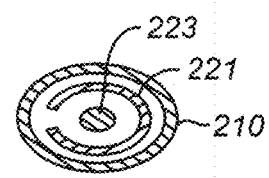

In cross-section, for example, the inner control mechanism 223 has a solid circular cross-section and is positioned to fit within the lumen 222 of the notched tubular member 221. As shown in FIG. 5D, which is taken across the lines D-D in FIG. 5B, the cross-section is taken across a notch 226 of the notched tubular member 221 and therefore the tubular member 221 has a partial circular cross-sectional shape, such as a "c." The tubular member 221 and inner control mechanism 223 fit within the lumen 212 of the sheath 210. As illustrated in FIG. 5F, when the inner control mechanism 223 is moved axially the notches 226 are brought together and the gap between the edges of the notches get smaller. Thus, for example, as shown in FIG. 5F, the partial circular cross-sectional shape shown in FIG. 5C becomes elliptically shaped for a cross-section taken perpendicular to the longitudinal axis L as the device 200 assumes the curved configuration shown in FIG. 5C and the cross-section of the notched tubular member 221 becomes an elliptically shaped, or substantially elliptically shaped, "c" with the edges closer to contact.

In the cross-section illustrated in FIG. 5E, which is taken along the lines E-E of FIG. 5B, the exterior of the proximal end of the notched tubular member 221 is configured to engage the interior of the proximal end of the sheath 210 in order to maintain a permanent or semi-permanent relationship between the two members (thus preventing rotational movement of the notched tubular member 220 without rotational movement of the sheath 210). In the cross-section of FIG. 5E, the parts are maintained by the use of one or more tongue and groove joints 218 that engage one component with another. Other mechanisms for engaging the sheath 210 and the notched tubular member 221 would be apparent to those skilled in the art, including, for example, the use of a detent on one member and depressions on another member to provide a snap fit arrangement.

Each of the sheath 210 and the notched tubular member 220 can have a flange 217, 227 to facilitate manipulation by the user and, in the case of the flange 227 of the notched tubular member 220, the flange 227 can provide a further mechanism for preventing the notched tubular member 220 from advancing entirely into the lumen 212 of the sheath 210 upon manipulation of the inner control mechanism 223.

In operation of the steering component, pulling or pushing the inner control member 223 in an axial direction 206 results in a deformation of the steerable member 220 away from a longitudinal axis L of the device 200. The amount of deviation of the distal end away from the central axis L is controlled by the user and the amount based on the amount of push/pull of the inner control of control member 223 of the steerable member 220. As the inner control member 223 is pulled proximally (i.e., pulled proximally toward the user and/or device controls), the angle α of the deviation away from the longitudinal axis L, is increased because the inner control member 223 pulls the sides deforming the notches 226 of the control member (as illustrated in FIG. 5C) which causes the steerable member 220 to bend in a direction and achieve movement that is, for example, 180°, or more, off the longitudinal axis in one or more planes. Additionally, one component can be pulled, while another component is pushed to achieve the same result.

The action of the user engaging the control mechanisms and/or flanges causes a bending force to be applied which results in the device steering toward a target site. As the bending force increases, the stress on the steerable member increases, which induces a curvature of the device. Thus, the strain occurs when the steerable member is distorted by the user engaging the control mechanism. The application of a bending force results in an active steering of the designs described in this invention, as opposed to passive steering resulting from deformation to a preformed shape. Combinations of active and passive steering can be used without departing from the scope of the invention. Further the curvilinear length of each component of the device can remain the same, or substantially the same, as the longitudinal length (for an unbent device) during the steering and advancing processes. The device is adapted and configured to define and create its own path to the target site. The definition and creation of a path can occur dynamically as the device is advanced through tissue. Thus, for example, as the device is advanced through tissue, the denseness, or other features, of the tissue may place a stress or strain on the device that causes the device to deviate away from a trajectory toward a target site. Controlling the location and direction of the distal end of the device by engaging the control mechanisms to place a strain, such as an opposing strain or bending force, on the device using the control mechanisms causes the device to steer toward the target site.

Thus, when advancing toward a target site, the entire mechanism (sheath 210 and steerable member 220) is advanced toward the target site. As the location of the device 200 relative to the target site is assessed (using, for example, an image capture machine 60 FIG. 3) and it is determined that the trajectory has deviated from the trajectory required to reach the desired target site (see, for example, FIGS. 2B-C), the steerable member 220 can be engaged to cause the distal end 204 of the device to maintain or deviate from the original trajectory by bending the distal end 204 of the device 200. As will be appreciated by those of skill in the art, the step of adjusting the control member 223 can be alternated as required to optimize accessing the target site. Additionally, a knob, such as those illustrated in other embodiments, can be provided at the proximal end and can be engaged to further provide rotational control of the device 200, providing up to 360° movement of the device around the longitudinal axis L. Separate movement of the sheath 200 relative to the control mechanism 220 can be achieved where the mechanisms are disengaged, e.g. where the tongue and groove are uncoupled, or the male and female threads are disengaged.

FIGS. 6A-E illustrate perspective and cross-sectional views of yet another steerable device 300 capable of accessing a target sample. In this embodiment, an optional sheath 310 is provided with a steerable member 320 positioned within at least a part of the lumen 312 of the sheath 310. The steerable member 320 has a control wire 324, or pull wire, adapted to engage the steerable member 320 at least at two points along its length. The control wire 324 can be used to cause a difference in location of the distal tip of the steerable member 300 during actuation. Thus, the wires can be thought of as differential wires for causing differences in the location of the tip of the devices. The control wire 324 has a length that is less than the length of the steerable member 320. The control wire 324 can be formed from a material having elastic properties in at least one direction. As the control wire 324 engages the interior surface 313 of the lumen 312 of the sheath 310, the control wire 324 is deformed which results a deformation of the steerable member 320. A knob 332 is provided at the proximal end 302 which in use can, directly or indirectly, control the axial 306 and rotational 308 movement of the steerable member 320 within the sheath 310. As will be appreciated by those of skill in the art, the control wire 324 can be in the form of a wire, having a circular cross-sectional shape (as illustrated), or can be in the form of a band or ribbon (e.g., flat strip having a square or rectangular cross-sectional shape), or any other shape that achieves the operational objectives of the device design.

Figure 6A:
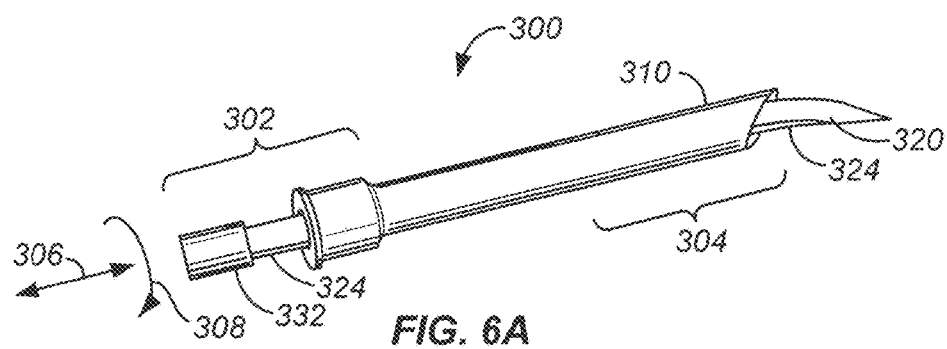
FIGS. 6A-E illustrate perspective and cross-sectional views of yet another steerable device capable of accessing target site or anatomic locations.
Figure 6B:
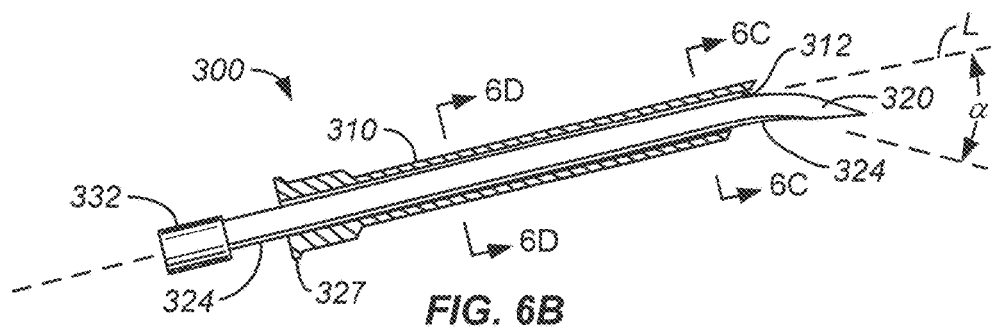
Figure 6C:
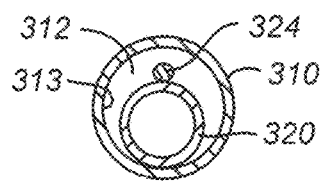
Figure 6D:
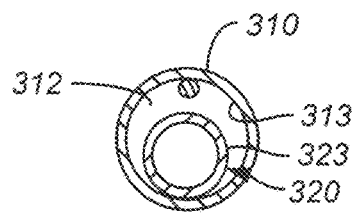

Turning to FIG. 6B, the steerable member 320 is in the form of a central beveled needle 340 with a single control wire 324, or pull wire, in the form of a guidewire attached to the steerable member. At portions along the length of the steerable member 320 the control wire 324 assumes a configuration whereby it is adjacent the interior wall or lumen 313 of the sheath 310, as shown in the cross-section of FIG. 6C, or bows away from the steerable member if no outer sheath is present. At other locations, the control wire 324 can assume a configuration whereby it is adjacent the surface of the steerable member 320. At still other locations, the control wire 324 can assume a configuration whereby it is positioned equidistant between the interior wall 313 of the sheath 310 and the surface 323 of the control wire 324. At yet other locations, the control wire 324 can assume a configuration whereby it comes in contact with both the interior lumen 313 of the sheath 310 and the exterior surface of the steerable member 320. As will be appreciated by those skilled in the art, the diameter of the interior lumen of the sheath 310 can be constant along its length or can vary along its length, to provide mechanical pressure on the control wire 324 and/or deform control wire 324.

In operation of the steering features, as the steerable member 320 is advanced in a distal direction and exits the distal end 304 of the sheath 310, the distal end of the steerable member 320 assumes a curved shape that deviates away (angle α) from a longitudinal axis L of the device 300 and which is controlled by the control wire 324. The amount of deviation away from the central axis L is controlled by the user, the amount of distance the distal end 304 of the steerable member 320 extends out of the sheath 310, as well as by the material properties of the control wire 324, such as elasticity, deformability, strength, etc. As the steerable member 320 is drawn back into the sheath 310 (i.e., pulled proximally toward the user and/or controls), the angle α is decreased because pressure is applied to the control wire 324 by the interior walls of the sheath 310 which causes the steerable member 320 to straighten out. Thus, when advancing toward a target site, the entire mechanism (sheath 310 and steerable member 320) can be advanced toward the tissue. As the location of the device 300 relative to the target site is assessed (using, for example, an image capture machine 60 discussed with respect to FIG. 3) and it is determined that the trajectory has deviated from the desired target site (see, for example, FIGS. 2B-C), the steerable member 320 can then be advanced distally toward the target site while maintaining the sheath 310 in a fixed, or largely fixed location, to enable the device 300 to reach the target site. As will be appreciated by those of skill in the art, the step of advancing the device 300, and advancing only the steerable member 320 can be alternated as required to optimize accessing the target site. In some instances, steering the device may occur actively while forming a curvilinear shape that is equivalent, or substantially equivalent, in length to the unbent length of the device. In addition to controlling the location of the device 300 by advancing the device 300 and/or the steerable member 320, further control can be achieved by rotating the knob 332 clockwise and counterclockwise.

In another operation, the control wire 324 is pushed or pulled as the flange 327 of the steerable member 320 is engaged. This action results in the steerable member 320 being held stationary with respect to movement of the control wire 324. A locking mechanism, as described above, can also be incorporated.

Figure 6E:
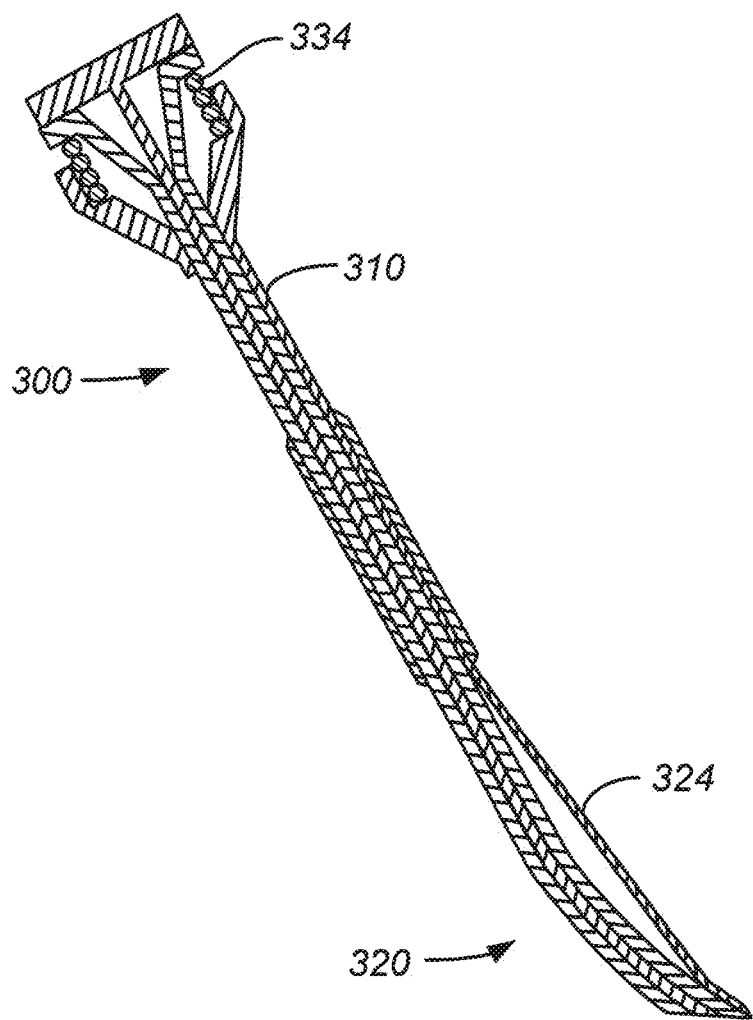

FIG. 6E illustrates an alternative cross-sectional view wherein a spring 334 is provided to increase the amount of control administered to the device 300.

FIGS. 7A-E illustrate perspective and cross-sectional views of still another steerable device 400 capable of accessing a target site. The device 400 illustrated in FIG. 7 includes the sheath 410, having a steerable member 420 arid a control member 430. Where the design of FIG. 6 provides a single control wire 424, the design of FIG. 7 uses more than one control wire 424, 424', or four control wires (as illustrated). A central steerable member 425, which can be in the form of a wire, and four lateral control wires 424, 424' are provided that engage a control lever 433. Movement of a tab 435 of the control lever 433 in a direction will result in controlled movement of the distal end of the device 400 causing the distal end of the device to curve toward a target area, such as target tissue, cells or fluids. The control wire can be metal, polymers, or organic fiber, such as carbon or aramid fibers (Kevlar®). Additionally, the control wire can be glass or ceramic.

Figure 7A:
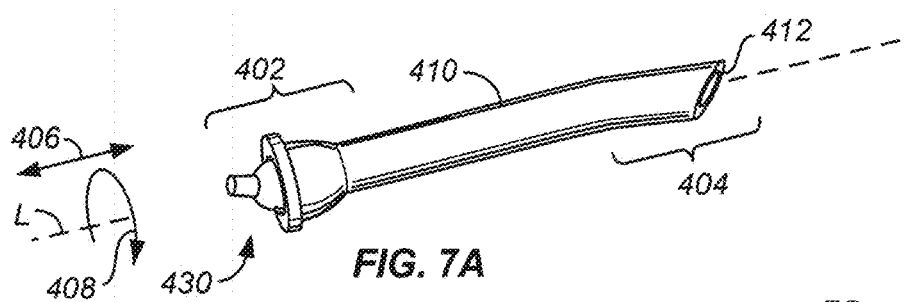
FIGS. 7A-E illustrate perspective and cross-sectional views of still another steerable device capable of accessing target site or anatomic locations.
Figure 7B:
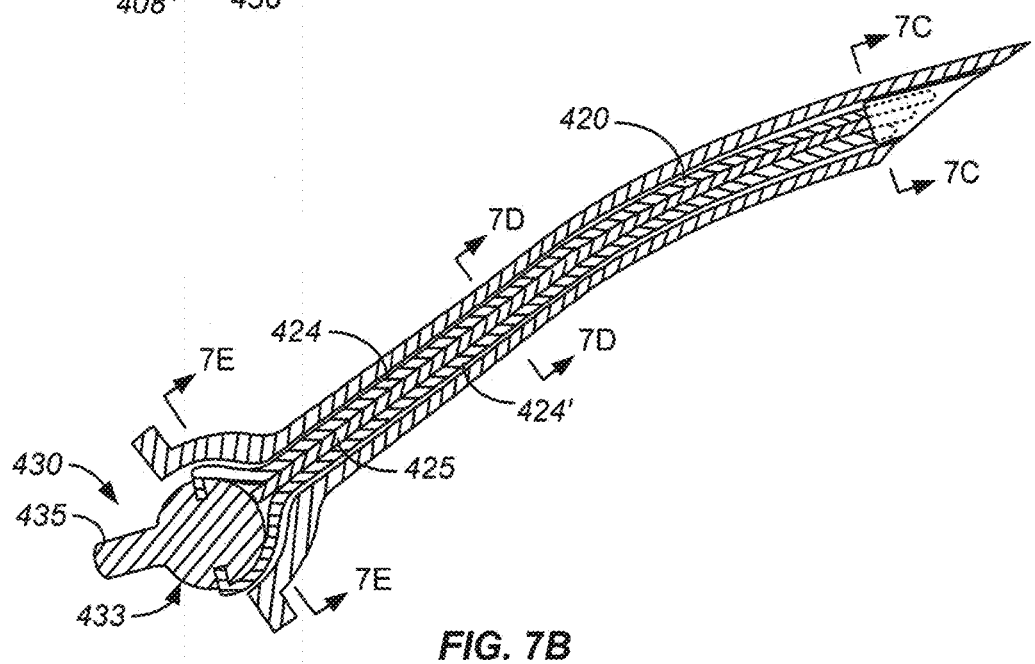
Figure 7C:
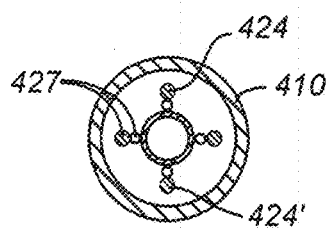
Figure 7D:
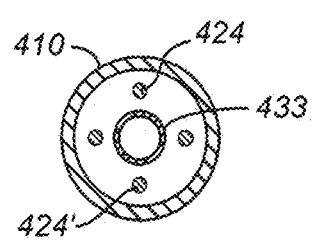
Figure 7E:
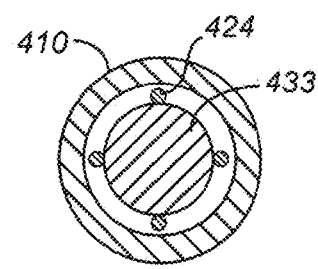
Figure 8A:
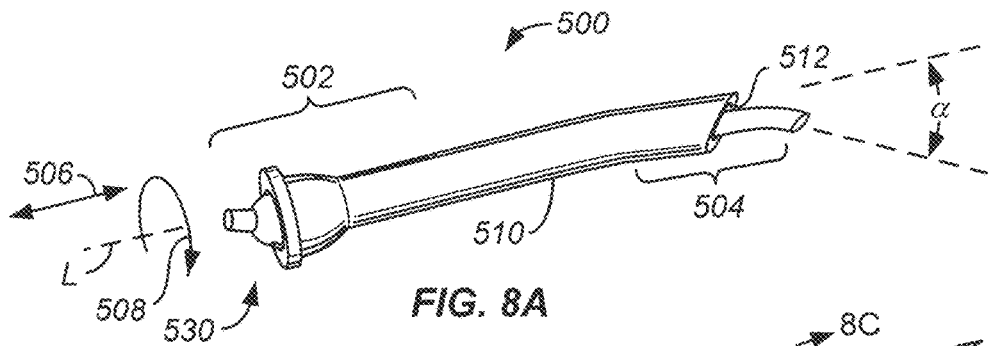
FIGS. 8A-E illustrate perspective and cross-sectional views of another steerable device capable of accessing target site or anatomic locations.
Figure 8B:
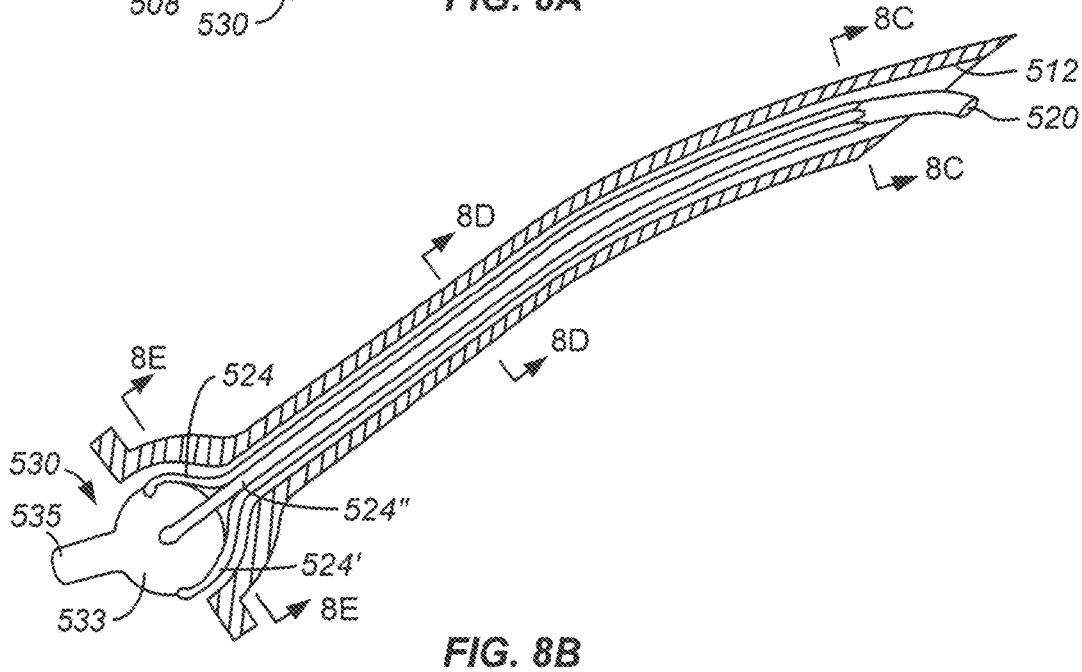
Figure 8C:
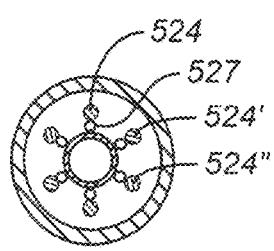
Figure 8D:
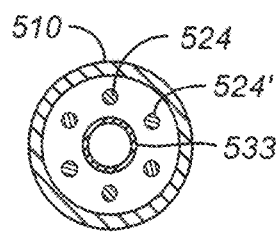
Figure 8E:
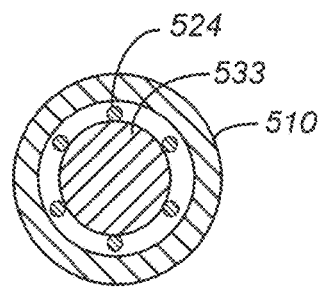

In operation of the steering features, for example, as the tab 435 is moved toward the right, the control wire 424 engaging the control lever 433 on the right will be advanced proximally causing the distal tip 404 of the device 400 to move toward the left (i.e., movement of the tab in a first direction will cause a movement of the distal end 404 of the device 400 in a direction opposing the directional movement of the tab). As illustrated in FIG. 7C the control wires 424, 424' can be soldered 427 to the exterior of the control lever 433. Additionally, or in place of soldering, the control wires 424, 424' can be crimped, glued, or combinations and/or configured to bend at a proximal end such that the proximal end can be placed within a lumen in the control lever 433. The operation of the steering features enables a one-handed, highly accurate, control of both the steering of the distal tip of the device and the advancement of the device along a path toward a target site.

Further, as discussed above, the action of the user engaging the control mechanisms and/or flanges causes a bending force to be applied which results in the device steering toward a target site. As the bending force increases, the strain on the steerable member which induces curvature increases. The application of a bending force results in an active steering of the designs described in this invention, as opposed to passive steering resulting from deformation to a preformed shape. Further the curvilinear length of each component of the device remains the same, or substantially the same, as the longitudinal length (for an unbent device) during the steering and advancing processes. The device is configured to create its own path to the target site. This design improves the usability, consistency and accuracy of operation of the device, as well as the ergonomic interface with a user and human factors design considerations.

FIGS. 8A-E illustrate perspective and cross-sectional views of another steerable device 500 capable of accessing a target sample. The device 500 illustrated in FIG. 8 includes the optional sheath 510, having a steerable member 520 and a control member 530. Where the design of FIG. 6 provides a single control wire 324, the design of FIG. 8 uses a plurality of control wires 524, 524'. The provision of additional control wires 524, 524' enables the control lever 533 to achieve more accurate control of the distal end 504 of the device 500. As will be appreciated by those skilled in the art, a knob 535, or other suitable mechanism, can be provided at the proximal end 502 in order to provide additional rotational movement to the device 500. The operation of the device of FIG. 8 is similar to the operation described with respect to the embodiment depicted in FIG. 7.

FIGS. 9A-E illustrate perspective and cross-sectional views of another steerable device 600 capable of accessing a target sample. In this embodiment the interior lumen of the distal end 604 of the sheath 610 is configured to curve or angle away from the longitudinal axis L, or further away from the longitudinal axis L than a section of the sheath proximal to the distal end. Thus, the distal opening 611 of the sheath 610 forms a bend 613 that results in the distal opening 611 being positioned such that it does not cross all, or part, of the longitudinal axis L.

Figure 9A:
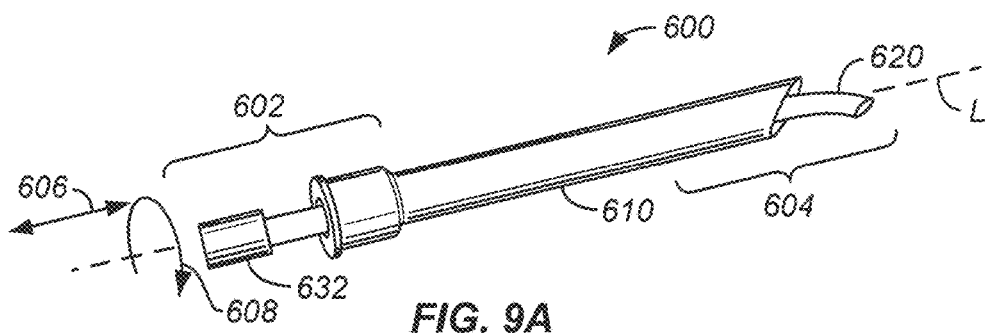
FIGS. 9A-E illustrate perspective and cross-sectional views of another steerable device capable of accessing target site or anatomic locations.
Figure 9B:
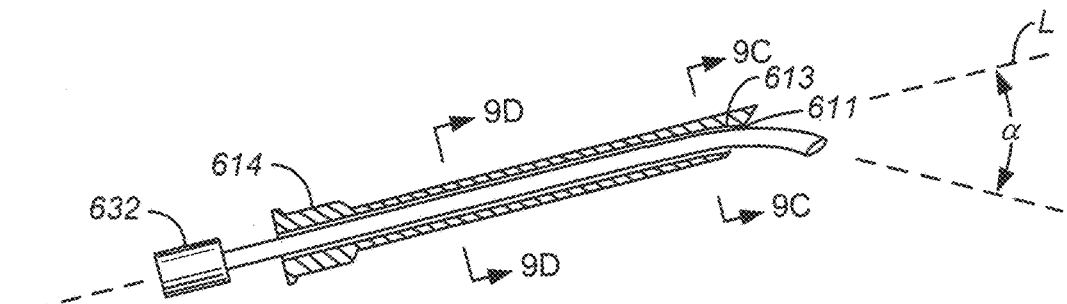
Figure 9C:
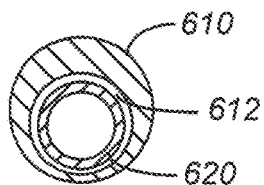
Figure 9D:
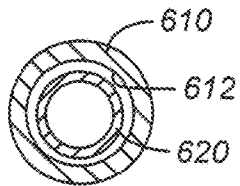
Figure 9E:
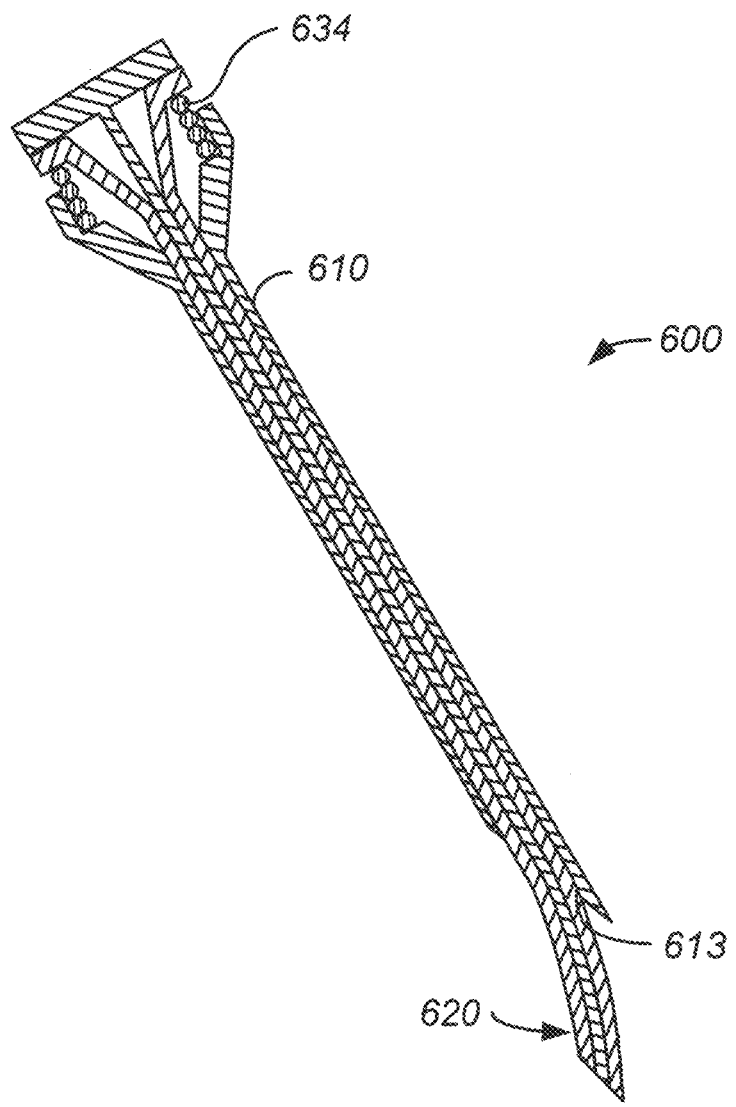

In operation of the steering features, as the steerable member 620 is moved in a longitudinal direction 606, the distal end of the steerable member 620 advances and causes the bend 613 in the interior of the lumen of the sheath 610 which, in turn, bends the steerable member 620 an amount corresponding to the bend in the interior lumen of the sheath 610. As the distal end of the steerable member 620 continues to advance through the lumen of the sheath 610 and extend beyond the distal end of the sheath, the steerable member is bent away from a central longitudinal axis L of the device in a predetermined or determinable amount. Further rotational movement 608 can be achieved by turning a control mechanism, such as a sheath knob 614 in a clockwise and/or counterclockwise direction. As illustrated by the cross-sections shown in FIGS. 9C-D, taken along an axis perpendicular to the longitudinal axis of the device 600, the lumen 612 of the sheath 610 is positioned at a first location (e.g. a midpoint along the length of the device) more centrally located than at a second location (e.g., a position at the distal end). Once the distal end of the control member 620 is advanced beyond the distal end of the sheath 610, rotational movement of the entire mechanism 600 can be achieved by engaging knob 632. As illustrated in FIG. 9E, the device 600 can be configured to include the use of a spring 634. Further the device 600 can be configured such that once the control wire 623 achieves the desired location, it can be removed, leaving an open lumen for administering another component (e.g. a diagnostic device or tissue biopsy device).

Figure 10A:
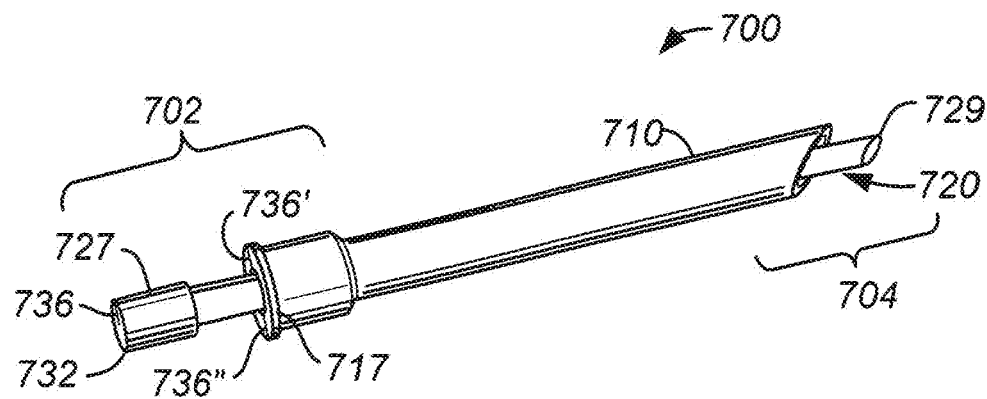
FIGS. 10A-C illustrate perspective and cross-sectional views of yet another steerable device capable of accessing target site or anatomic locations.
Figure 10B:
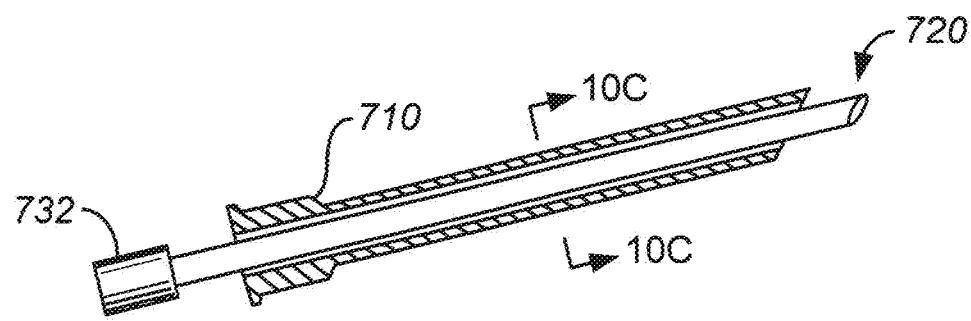
Figure 10C:
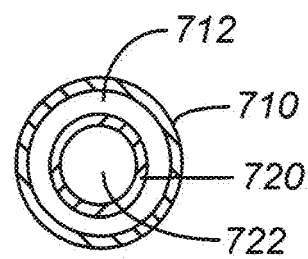

FIGS. 10A-C illustrate perspective and cross-sectional views of yet another steerable device 700 capable of accessing a target sample. The device 700 has an outer sheath 710 having a lumen 712 into which a steerable member 720, such as a stylet, is received. The steerable member 720 engages a top cap or knob 732 which includes a position indicator 736 (as depicted, position indicator 736 is an arrow provided on a surface of the knob 732). Additional indicator markings can be provided on a lip or flange 717 of the outer sheath 710, such that the position indicator 736 is relative to one or more markings 736', 736" on the flange 717, thus giving a relative direction or movement of the stylet 720 relative to the device 700 or sheath 710. In this embodiment, like the embodiment shown in FIG. 4, the steerable member 710 has a flexible curved distal tip that reforms (or returns to a curved configuration) upon advancing the steerable member 710 beyond the distal end of the outer sheath 710. As will be appreciated by those skilled in the art, markings can be provided on any of the other designs provided for herein without departing from the scope of the invention. The style of the position indicator(s) can also be modified, as desired. For example, in an indication of degrees in one or more directions could be included, as well as, or in addition to, the arrow markings Additional markings could be provided on the stem of, for example, the steerable member or outer sheath, to provide additional indications of movement in an additional plane.

In an embodiment of the markings, an arrow position indicator is provided that corresponds to, for example, a pointed tip 729 of the stylet. A thicker and thinner (top-bottom) indicator 736', 736" can be provided on the flange 717 to enable the user to determine the location of the pointed tip 729 of the stylet relative to the sheath 710. The pointed tip can also be configured to correlate to the exterior curve of the stylet once the stylet is advanced beyond the end of the distal tip of the outer sheath. The knob 732 can further be configured to engage the proximal end of the outer sheath 710 such that the position of the flexible member 720 is locked in place. For example, tongue and groove, detents and channels, or any other suitable design or configuration can be used to engage one component with another. The implementation and design of the markings can be modified to incorporate human factors considerations.

In operation, a user would use the position indicators 736 to determine the orientation of the tip of the device relative to the target site. Further steering could be accomplished based on, for example, determination by reviewing an image that the device needed to be advanced, for example, to the right 10° in order to engage the tissue. Using the position indicator(s), the user would steer the distal tip of the device (located within the patient) in a manner to achieve the desired movement and advance the device toward the target site.

Figure 11A:
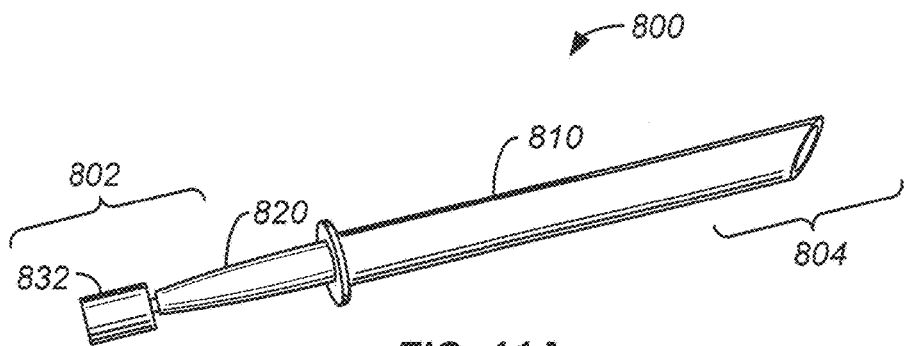
FIGS. 11A-G illustrate perspective and cross-sectional views of still another steerable device capable of accessing target site or anatomic locations.
Figure 11B:
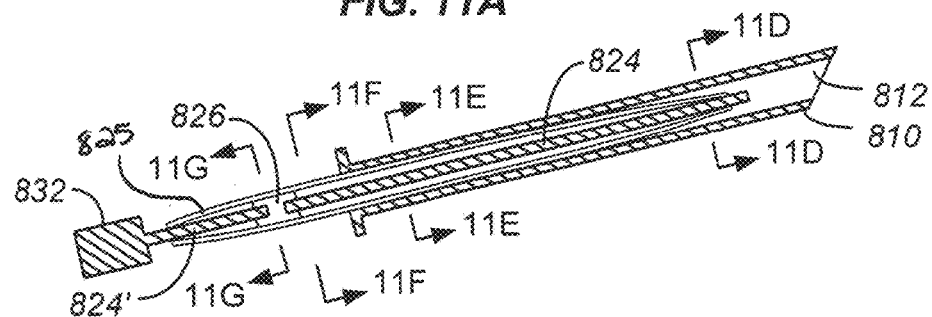
Figure 11C:
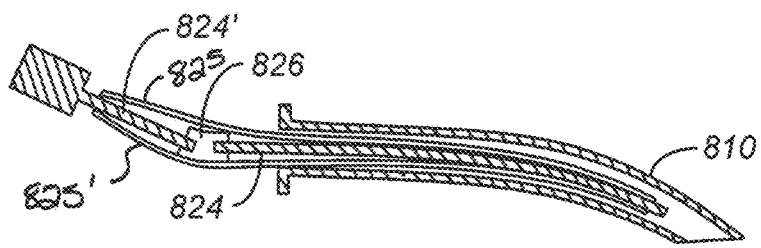
Figure 11D:
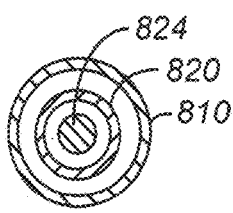
Figure 11E:
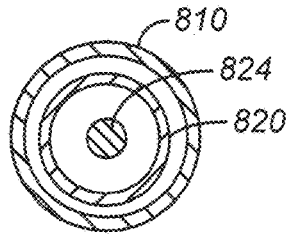
Figure 11F:
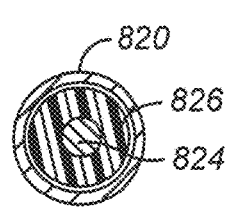
Figure 11G:
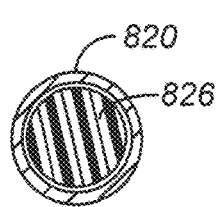

FIGS. 11A-G illustrate perspective and cross-sectional views of still another steerable device 800 capable of accessing a target sample. The device 800 has an outer sheath 810 and an inner steerable member 820. The inner steerable member 820 has a further lumen 822 which engages a steerable central wire 824 having two, or more, connectable sections 824', 824". As illustrated the steerable central wire 824 has two components which are connected near a proximal end by a flexible joint 826. The flexible joint 826 enables the components to be in flexible relationship with each other such that when the steerable member 820 is advanced distally, bending or rotation of a proximal end of the device 800 will result in steering of the distal end 804. As illustrated in FIG. 11C, the knob 832 is moved in a first direction which causes a bending of the distal end of the device 800. As shown in a cross-section taken perpendicular to a longitudinal axis of the device at a distal position, the cannula portion or control wire 824 can be positioned within a steerable sheath 820 which, in turn, fits within the outer sheath 810. In an alternative embodiment, the cannula portion 824 can be fitted within one or more steering wires 825, 825' as shown in FIG. 11B. The wires can be used to assist in the steering motion of the device by effecting differential lengths of the wires. For example, the embodiments illustrated in FIGS. 7-8 also use wires in the steering mechanisms. The lumen 822 into which the cannula 824 fits increases in size relative to the cross-section of the cannula 824 at a location proximal to the cross-section taken at D-D shown in FIG. 11D. This relationship is illustrated in FIG. 11E which is from a cross-section taken at E-E in FIG. 11B. As shown in FIG. 11F, a first section of the cannula 824', at its proximal end, engages a flexible material or joint 826 which enables the first section of the cannula 824' to move about an axis relative to a second section of the cannula 824" which engages the proximal control mechanism, or knob 832. At least a portion of the device 800 has a flexible sheath 810 that does not surround a cannula, as shown at the cross-section G-G depicted in FIG. 11G.

In steering the device, the operation of the device 800 is similar to the devices described above. However, the two piece structure of the steerable member 820 results in the proximal end of the device being rotatable relative to the distal end of the device about the joint. The amount of rotational movement achievable could be controlled by the flexibility of the material used at the joint. Additionally, flexibility could be lowered by advancing the steerable member into the outer sheath, thereby positioning the joint section of the steerable member within the outer sheath at a location where the flexibility of the joint is reduced.

As will be appreciated by those skilled in the art, the operation of the device can be such that the steerable member is positioned wholly or partially within tissue as the device operates and engages in steering and longitudinal movement as the device advances toward a target site. Additionally, or alternatively, the steerable member can be positioned wholly or partially within another member, such as the optional sheath or a scope, which itself is adapted to penetrate tissue, as well as engage in steering movement.

Figure 12A:
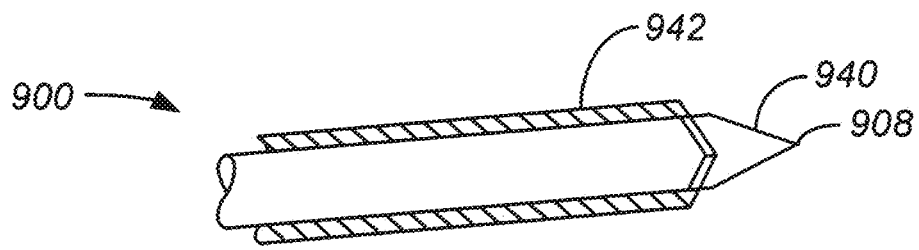
FIGS. 12A-C illustrate cross-sectional views of a variety of distal tip designs suitable for use with any of the steerable devices shown in FIGS. 4-11.
Figure 12B:
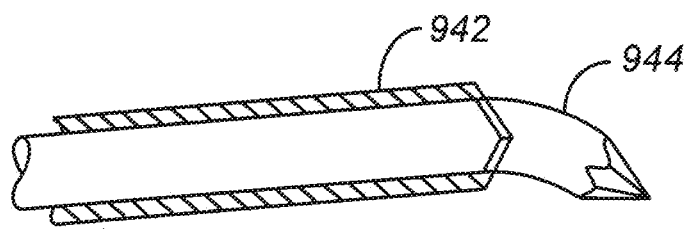
Figure 12C:
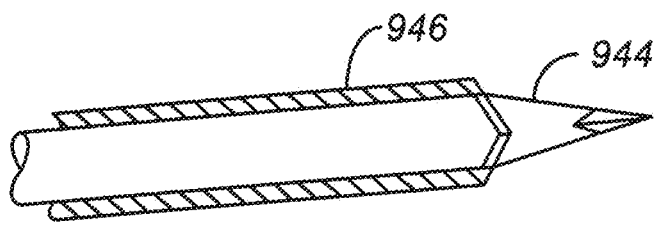

FIGS. 12A-C illustrate cross-sectional views of a variety of distal tip designs 900 suitable for use with any of the steerable devices shown in FIGS. 4-11. As will be appreciated, the tip designs 900 can be cannulated (thus providing a lumen within the center of the tip), or form a solid needle. The distal tip can also form a cutting apparatus, or be configured to provide therapeutic or diagnostic delivery mechanisms. As shown in FIG. 12A, a two-beveled needle dual needle or coaxial configuration is provided with a bevel core that is constrained within a needle. A first needle 940 fits within a second cannulated needle 942. In the embodiment illustrated in FIG. 12B a four-beveled core needle 944 is provided within a cannulated needle 942. FIG. 12C illustrates a four-beveled core needle 944 within a cannulated four-beveled needle 946. Other designs and embodiments can be used without departing from the scope of the invention. Further it will be appreciated that the core needle configuration can correspond to any of the steerable member designs described above, and the cannulated needle can correspond to the outer sheath configurations described above. Additionally, the central core needle, in addition to being cannulated, can be configured to be removable, alone or in combination with the sheath, to allow a device to be positioned within the lumen of the outer sheath. For example, a therapeutic, diagnostic or biopsy device could be positioned within the lumen.

Figure 13A:
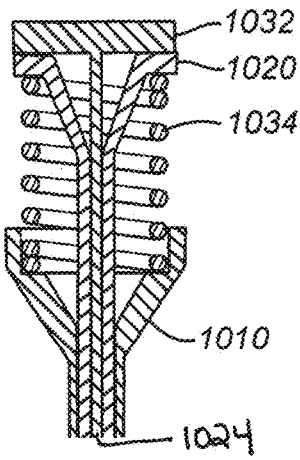
FIGS. 13A-F illustrate cross-sectional views of a variety of proximal control designs suitable for use with any of the steerable devices shown in FIGS. 4-11.
Figure 13B:
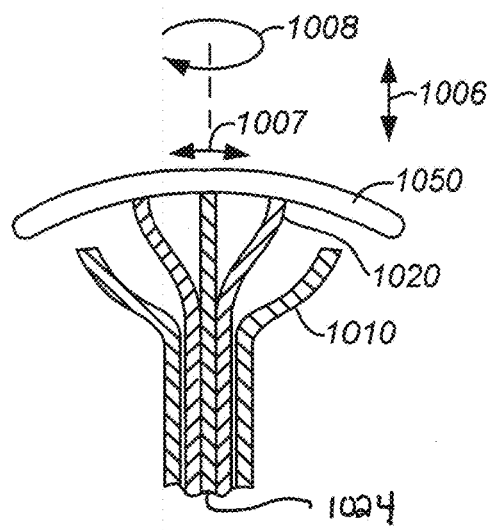
Figure 13C:
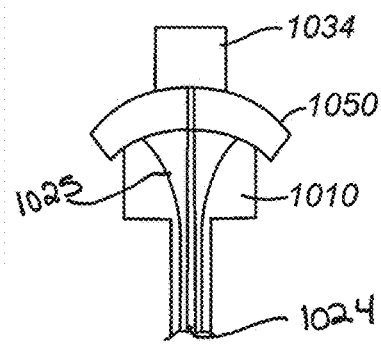
Figure 13D:
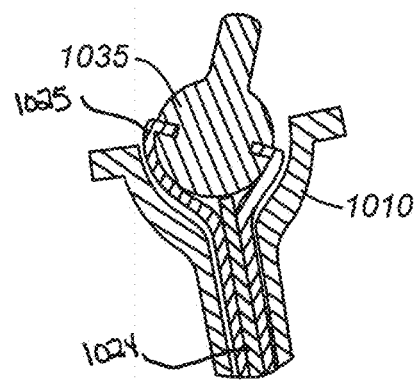
Figure 13E:
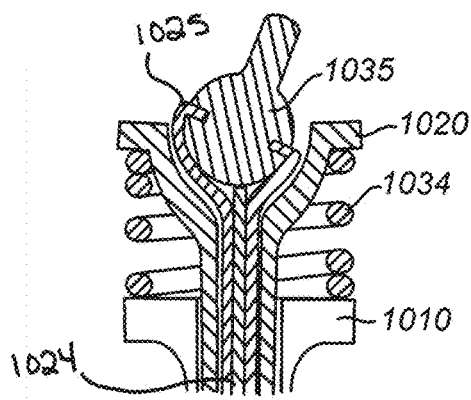
Figure 13F:
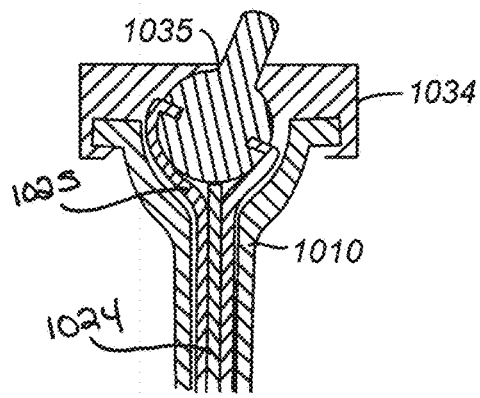

FIGS. 13A-F illustrate cross-sectional views of a variety of proximal control mechanisms suitable for use with any of the steerable devices shown in FIGS. 4-11, the proximal control mechanisms can be directly controlled by a user (such as a physician or technician), or can be engaged by another mechanism that enables the user to control the devices from a distance (e.g., another room). Luer fittings can also be provided at the proximal end of the device to facilitate control and engagement of various components. In the first embodiment, the outer sheath 1010 (corresponding, for example, to 110, 210, 310, 410, 510, 610, 710, 810, 910) engages a coiled member or spring 1034 (corresponding, for example, to 134, 334, 634). The coiled member 1034 provides control of the longitudinal movement 1006 along an axis of the steerable member 1020 (corresponding, for example, to 120, 220, 320, 420, 520, 620, 720, 820, 920) of the device as well as curved movement (e.g., where the coils are compressed on one side, and not the other and the distal tip deviates away from a longitudinal axis by an angle). FIG. 13B illustrates a handle 1050 which can provide additional forward and backward 1006, side to side 1007, or rotational 1008 motion of the steerable member 1020 relative to the outer sheath 1010. FIG. 13C illustrates the handle of FIG. 13B in combination with a knob 1034 that facilitates rotational movement of the steerable member 1020. FIG. 13D illustrates a rotational ball or tab 1035 in combination with wires of a steerable member 1020, wherein the wires are connected to the ball or tab 1035 in such a way that swiveling the ball in any direction off a central axis results in movement of the wires within a lumen of the outer sheath 1010 and a movement of the steerable distal end 1004 of the device. The device of FIG. 13E illustrates the rotational ball in combination with a coiled member 1034 or spring that can provide additional control of the longitudinal/axial movement of the device. FIG. 13F illustrates the rotational ball in combination with a knob 1034 which provides additional rotational control of the device. The embodiments employing a ball or tab 1035 facilitate single-handed steering and control of the device, as discussed above.

Figure 14A:
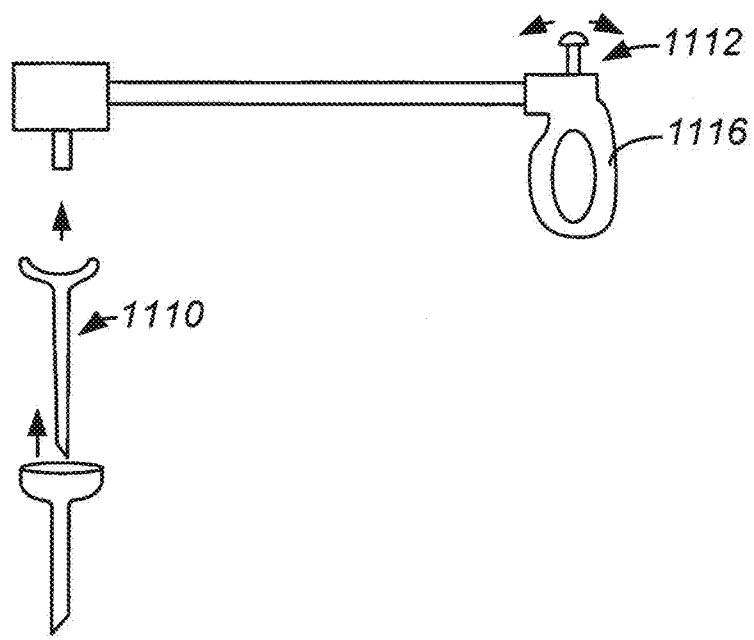
FIGS. 14A-B illustrate mechanisms for remote control of the steerable devices shown in FIGS. 4-11.
Figure 14B:
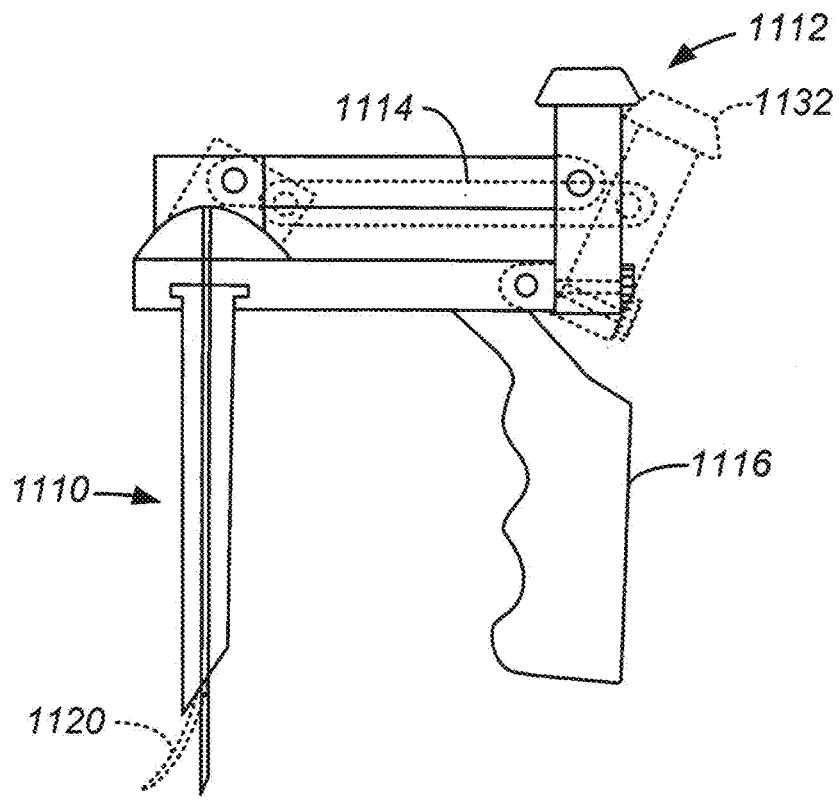
Figure 16:
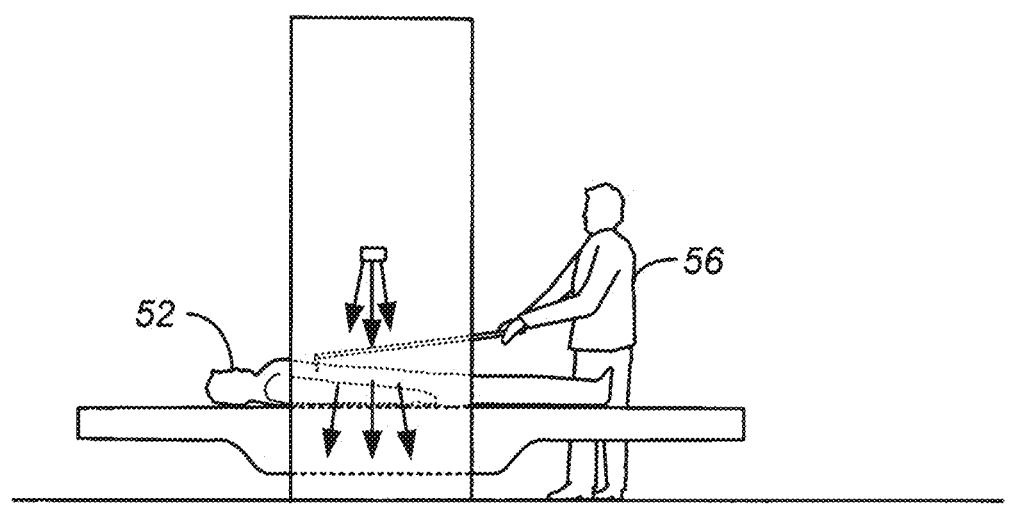
FIG. 16 illustrates a physician or technician controlling the steerable devices shown in FIGS. 4-11 to access target site on a patient using, for example, remote access devices shown in FIGS. 14 and 15.

FIGS. 14A-B illustrate mechanisms for remote control of the steerable devices shown in FIGS. 4-11. The configuration allows for real-time or near real-time guidance of the distal tip. An actuation lever 1112 is connected to a linkage within a handle 1116. The linkage within the handle 1116 communicates with an actuator that is connected to steerable member 1110. This enables control of the devices described above without the interventionalist (such as x-ray technician or physician) being in contact with the exterior of a patient's body during the assessment of where the device is positioned to access the target site. As a result the steering action for the device can be performed remotely from the needle site entry. Thus, by separating the position of the user's hand from the needle entry site, a CT-scan can be performed while operating the steerable device without radiation exposure to the user's hands, as shown in FIG. 16. In another embodiment, shown in FIG. 14B, a mechanism is provided for full gambling control remote from the radiation. A thumb knob 1132 is provided in the handle that allows a forward and back control of the steerable device. Additionally, a side to side movement and rotation is enabled as well, and combinations thereof, to optimize the movement of the distal end of the steerable device.

Figure 15A:
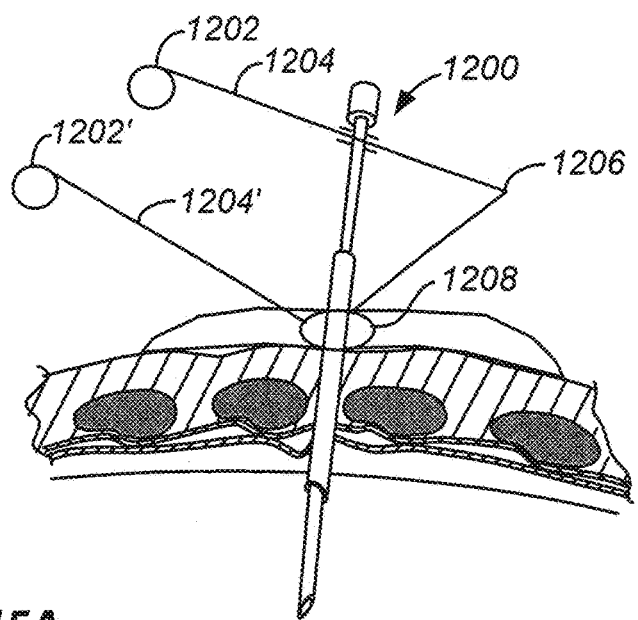
FIGS. 15A-B illustrate additional mechanisms for control of the steerable devices shown in FIGS. 4-11.
Figure 15B:
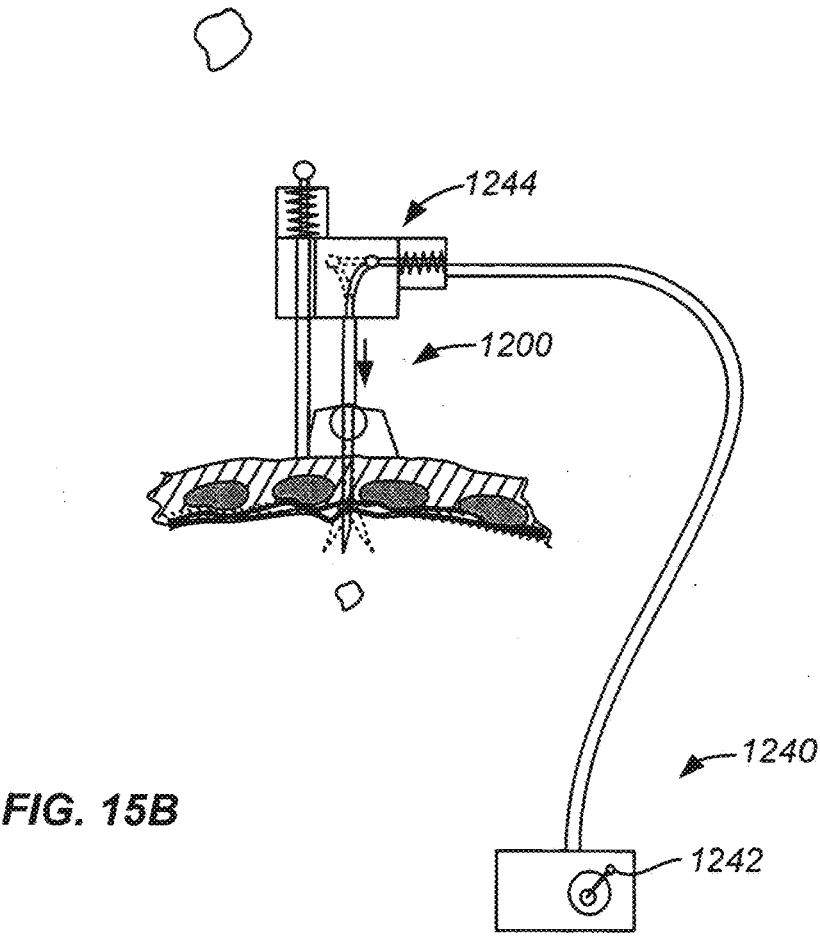

FIGS. 15A-B illustrate additional mechanisms for control of the steerable devices shown in FIGS. 4-11. In the embodiment shown in FIG. 15A, finger rings 1202, 1202' connected to control wires 1204, 1204' that pass through a passage formed in the proximal end of steerable device 1200. A hinge 1206 then attaches to a pivoting connection to a self-aligning bearing or ball gimbal 1208. The ball gimbal provides rotational freedom about two perpendicular axes. The second control wire extends from ring 1202' to a fixed connection on ball gimbal 1208. Ball gimbal 1208 is connected to control wires (not shown) as part of a steering mechanism for steerable device 1200 as described above. The distal end of the steerable device 1200 may be moved steered by moving rings 1202, 1202'. Steerable device 1200 may be advanced into the patient toward a suspected lesion by moving ring 1202 down toward ring 1202'. The entire apparatus may be attached to the patient's body by any suitable mechanism, including, for example, adhesive. The system illustrated in FIG. 15B illustrates a remote control apparatus 1240 that communicates with the steerable device 1200 using a joy stick 1242 that rotates around a pivot so that the distal point moves across a surface. The joy stick 1242 is connected to a linkage 1244 that can move to the left and right, as well as forward and back using push/pull control wires, thereby bending the steerable needle.

FIG. 16 illustrates an interventionalist 56, e.g. physician or technician, controlling the steerable devices shown in FIGS. 4-11 to access target site on a patient 52 using, for example, remote access devices shown in FIGS. 14 and 15. As will be appreciated by those skilled in the art, the remote access and control can be from a position that is in another room (as illustrated in FIG. 3), or from any suitable location, such as those that minimizes exposure to the image capture machine. Additionally, remote control wireless devices and mechanisms can be used by the interventionalist 56 to control the active steering and movement of the device. See, for example, U.S. Pat. No. 6,768,425 entitled Medical Apparatus Remote Control and Method (Flaherty et al.); and U.S. Pat. No. 6,577,893 entitled Wireless Medical Diagnosis and Monitoring Equipment (Besson et al.).

Figure 17:
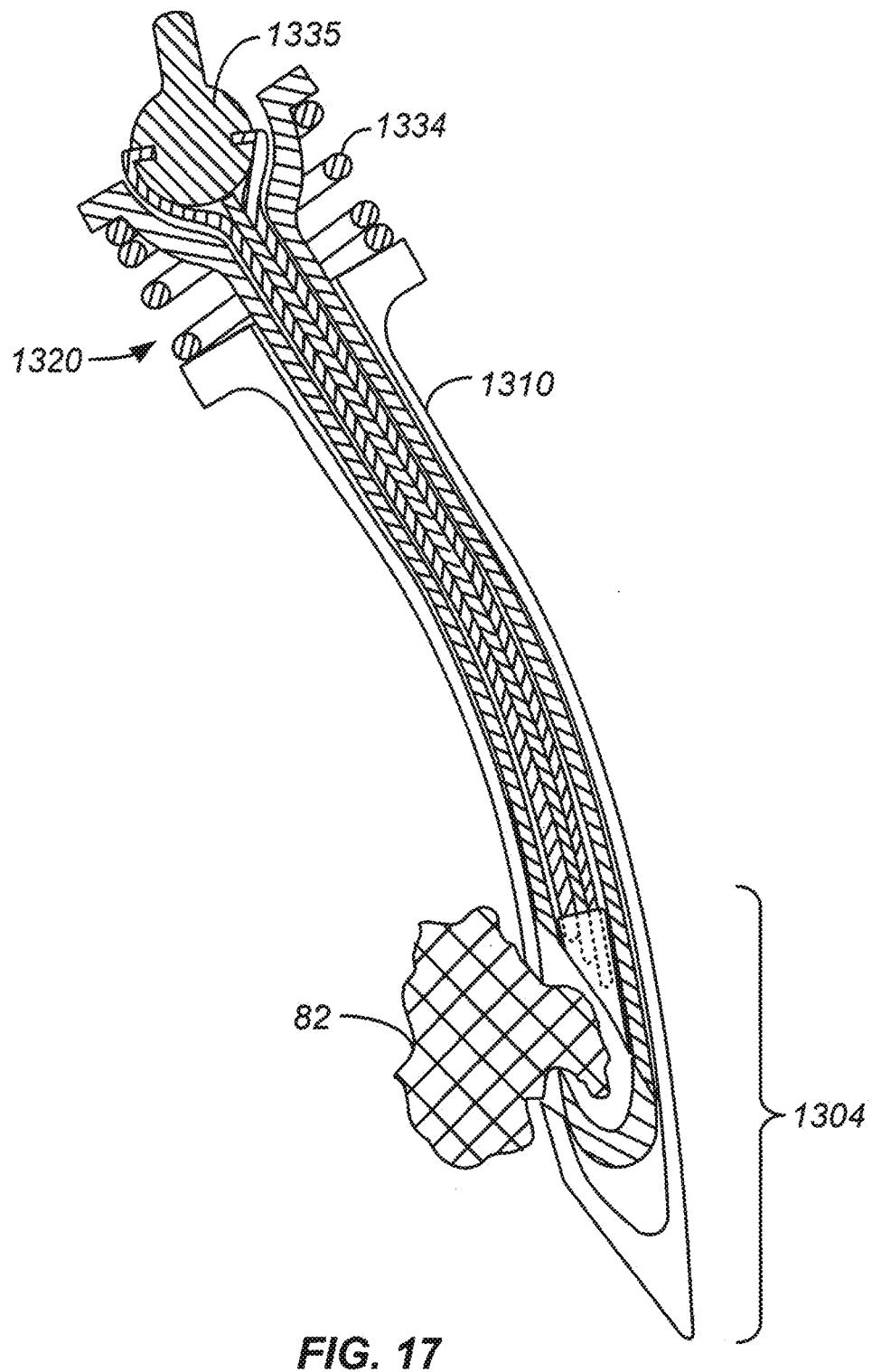
FIG. 17 illustrates a cross-sectional view of a steerable device used as a biopsy device to capture a tissue sample at its distal end.

FIG. 17 illustrates a cross-sectional view of a steerable device used as a biopsy device to capture a target sample at its distal end. In this embodiment, the outer sheath 1310 surrounds a steerable member 1320 which has a distal end configured to capture tissue 82. The steerable proximal end, uses a spring 1334 to control axial movement and a knob 1335 to control steering and bending of the distal end 1304 of the device. Modifications to the capture design of the distal end to facilitate collection of cells or fluid can also be made without departing from the scope of the invention.

Figure 18A:
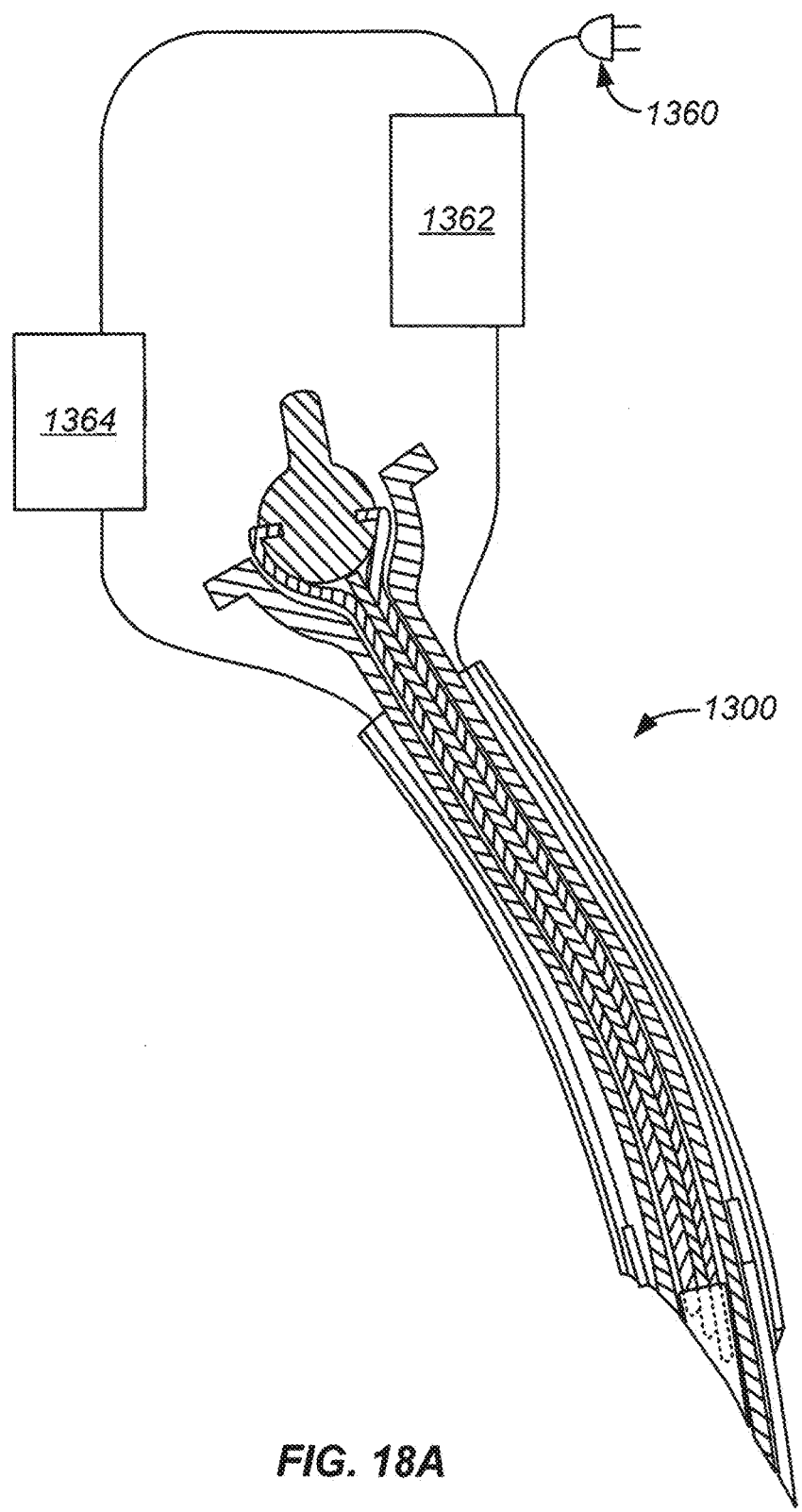
FIGS. 18A-C illustrate a variety of systems for controlling temperature sensing and delivery of heat or cold (FIG. 18A); temperature sensing and delivery of energy to produce heat and throttling gas to extract heat (FIG. 18B); and delivery of RF for cutting and coagulation (FIG. 18C) used in connection with the steerable devices shown in FIGS. 4-11.
Figure 18B:
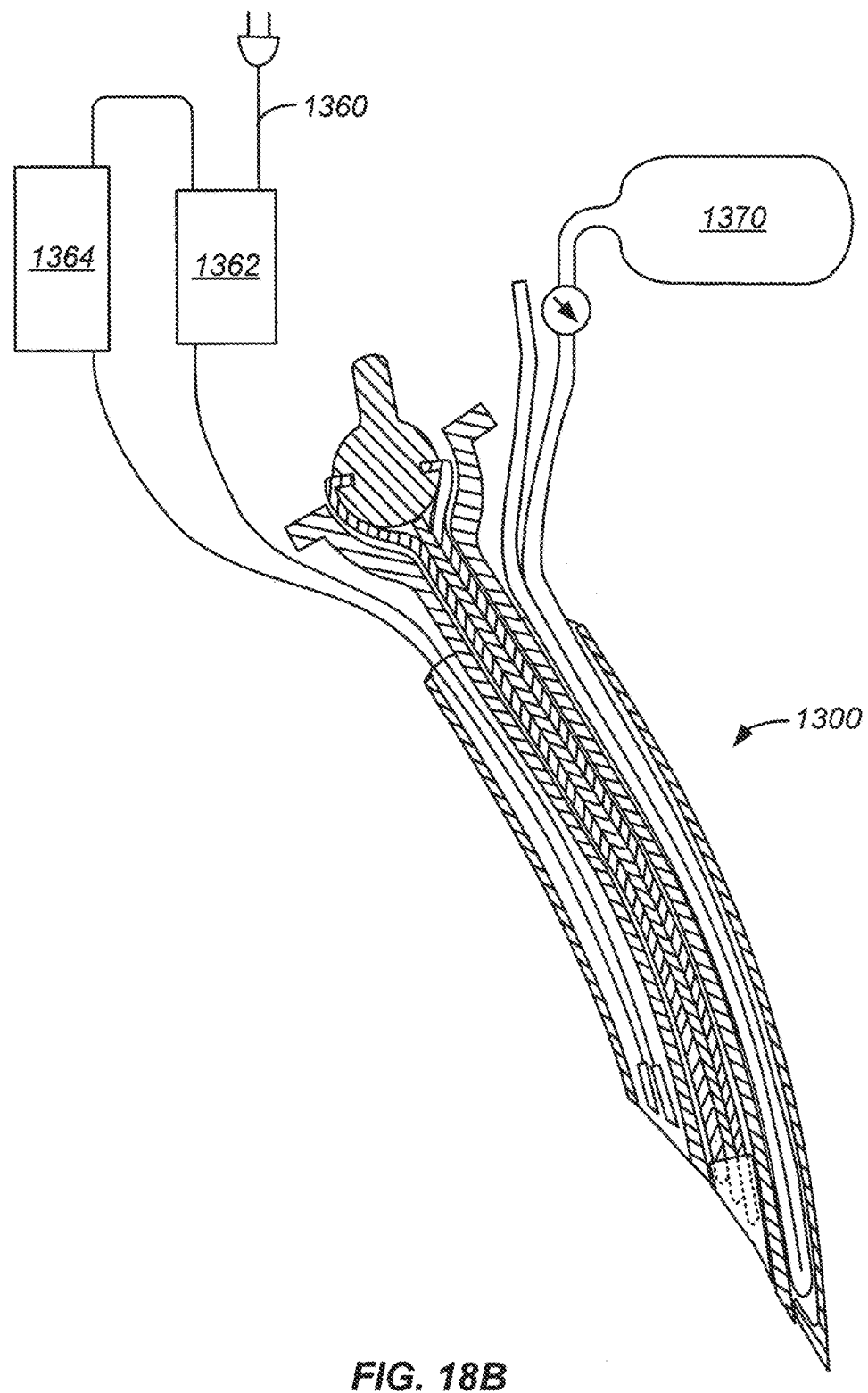
Figure 18C:
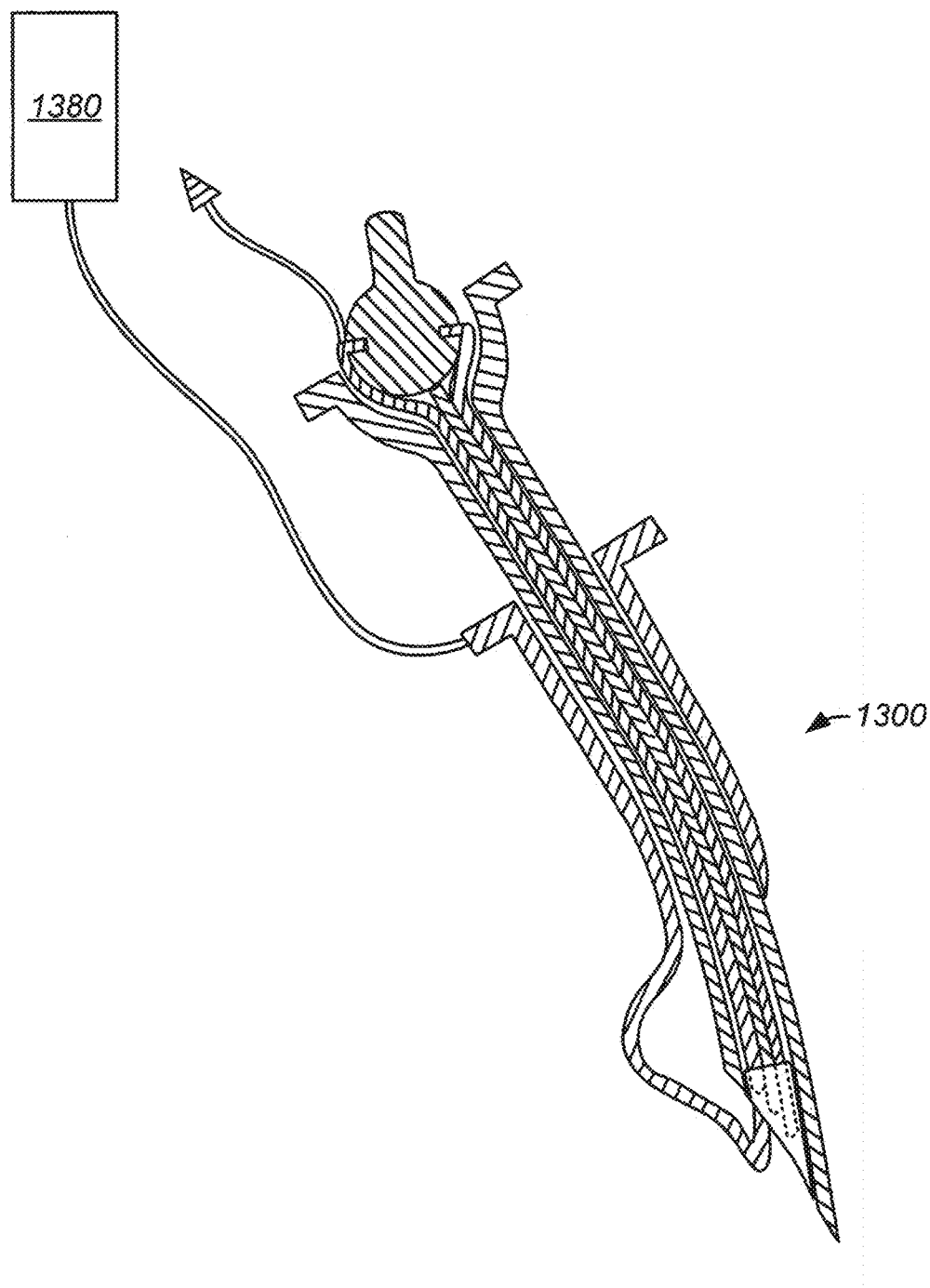

FIGS. 18A-C illustrate a variety of systems that can be incorporated in configuration and use of the device described above. For example, a mechanism for controlling temperature sensing and delivery of heat or cold, as illustrated in FIG. 18A can be provided. An energy source 1360 is provided that communicates with an energy delivery source 1362. The energy delivery source 1362 can deliver heat and/or cold. A sensor 1364 can also be provided to provide a loop to the system that controls application of further heat and/or cold. In another embodiment, the energy delivery source 1362 and sensor 1364 can be provided with a system for delivering pressurized gas 1370 as illustrated in FIG. 18B. In yet another system, such as that illustrated in FIG. 18C, a power supply 1360 can be provided that delivers RF energy to the distal tip of the device 1300, which results in cutting or cauterization of tissue and delivery of RF for cutting and coagulation. Any of these systems can be used in connection with any of the steerable devices shown in FIGS. 4-11.

Suitable materials for making the devices, and any component part of the devices, including those discussed above and disclosed herein, would be apparent to those skilled in the art. Suitable materials include biocompatible materials such as inorganic materials (metals, ceramics, and glasses) and polymeric materials (synthetic and natural). Thus, for example, stainless steel, shape memory alloys (such as nickel-titanium alloys) would be suitable for use in the device. Additionally, suitable polymeric materials can be selected from a wide variety of known biocompatible and biodegradable polymers, such as those classified as polystyrenes, polyphosphoester, polyphosphazenes, aliphatic polyesters and their copolymers, such as polycaprolactone, hydroxybutyric acid, and butylenes succinate. Other polyesters, such as nylon, and natural polymers, such as modified polysaccharides, may also be appropriate, depending upon the application. In some instances, it may be desirable to use a shape memory polymer that has the ability to store and record large strains. Still other polymers include polyetheretherketone, polyetherketoneketone, polyethylene, fluoropolymers, elastomers and the like.

Other appropriate polymers that can be used in the components or devices are described in the following documents, all of which are incorporated herein by reference: PCT Publication WO 02/02158 A1, dated Jan. 10, 2002 and entitled Bio-Compatible Polymeric Materials; PCT Publication WO 02/00275 A1, dated Jan. 3, 2002 and entitled Bio-Compatible Polymeric Materials; and PCT Publication WO 02/00270 A1, dated Jan. 3, 2002 and entitled Bio-Compatible Polymeric Materials. Still other materials such as Bionate®, polycarbonate urethane, available from the Polymer Technology Group, Berkeley, Calif., may also be appropriate because of the good oxidative stability, biocompatibility, mechanical strength and abrasion resistance. Combinations of any suitable material, including the materials listed here, can be used as well, without departing from the scope of the invention.

Figure 19:
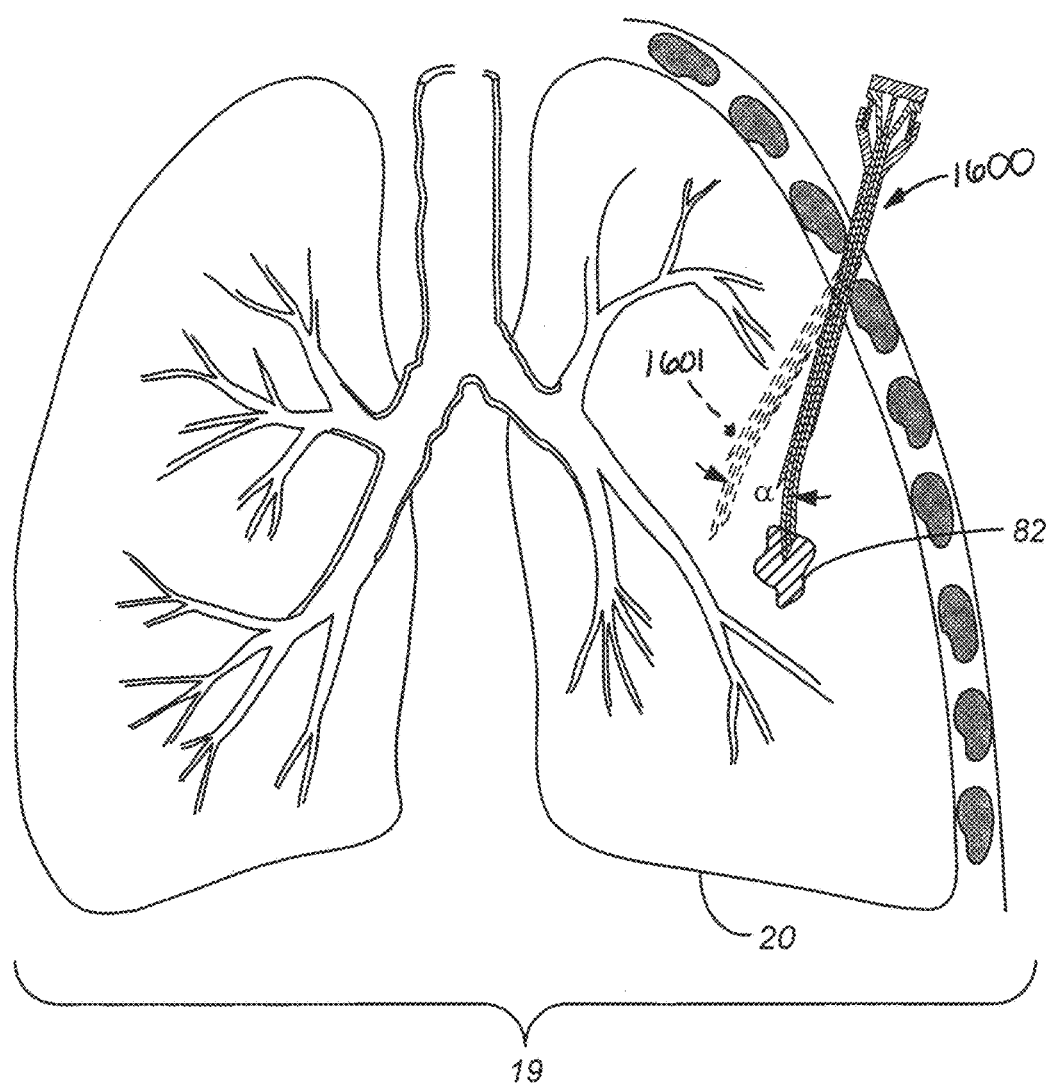
FIG. 19 illustrates a lung having a steerable device positioned to access a target site.

FIG. 19 illustrates a target lung 20, of lungs 19, having a steerable device 1600 positioned to access a target site 82. The device 1600 has been steered away from a first trajectory (the device shown in phantom) 1601, using the steering capabilities described above. As a result the steerable device 1600 engages the target site 82, whereupon any of the diagnostic, therapeutic, and marking procedures described above can be achieved using the steering device. The fact that the device 1600 creates its own path, which is steerable and correctable actively while advancing the device toward the target site, enables the device to be advanced to the target site without the need to repeatedly withdraw and re-advance the device. In the context of the lung, this simplified method decreases the likelihood that a pneumothorax will result.

Figure 20:
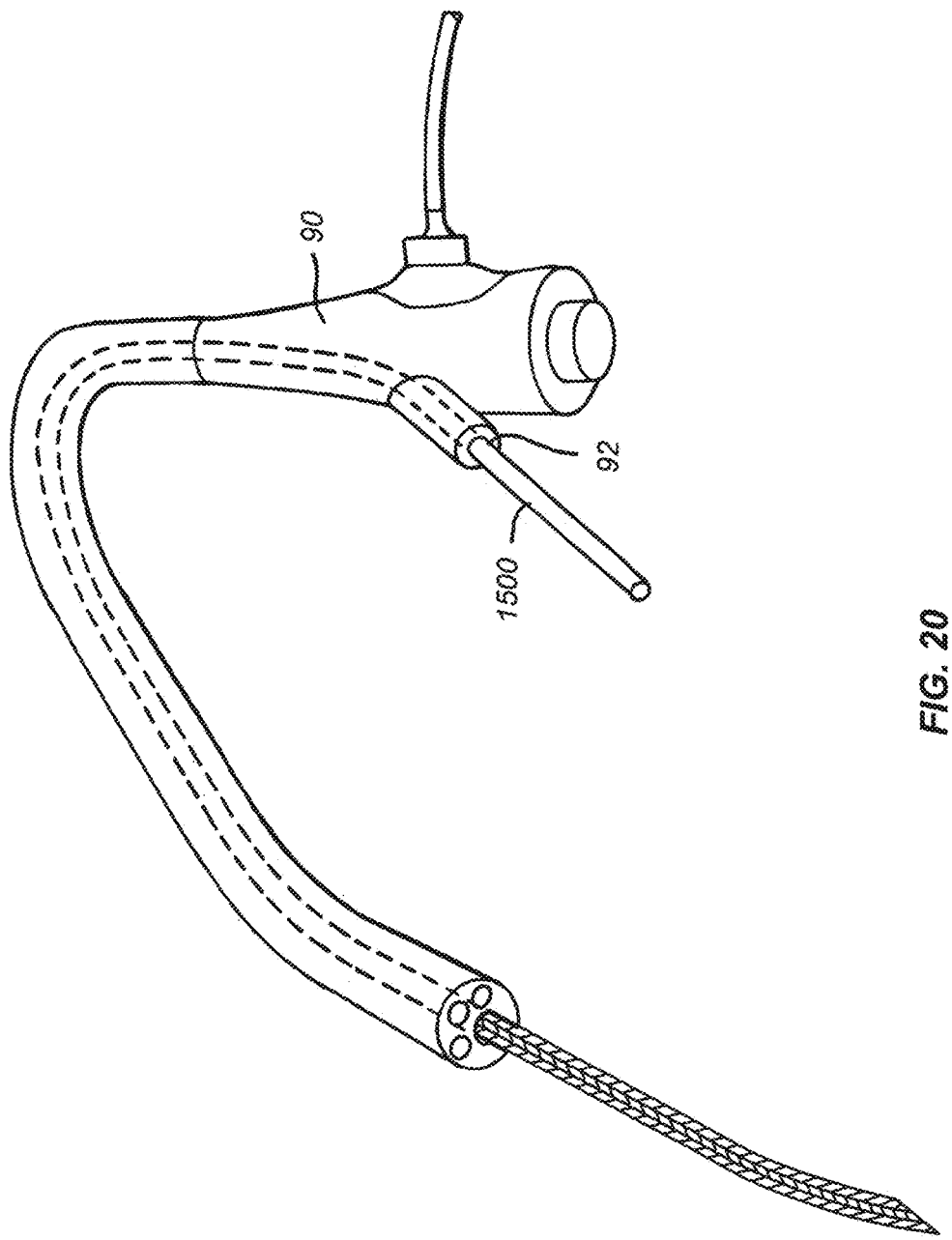
FIG. 20 illustrates a bronchoscope in combination with a steerable device.

For purposes of illustrating the use of the devices disclosed herein with a scope, FIG. 20 illustrates a flexible bronchoscope 90 with a working channel into which a steerable device 1500 has been inserted. The steerable device 1500 has been illustrated in a curved orientation which would result during operation using the devices and methods discussed above. As will be appreciated by those skilled in the art, prior to inserting the bronchoscope 90 into a patient, an access accessory, such as a guide wire (not shown) can be inserted into the distal end of the scope. The guide wire can then be bent around the scope end so that the guidewire lies outside the scope along the length of the scope. When the bronchoscope is inserted into a patient's lungs, the proximal end of the guidewire remains outside the patient. The guidewire can, however, be used to deliver diagnostic, therapy, or biopsy tools to the distal end of the bronchoscope without having to pass the tools through the working channel. These tools can be delivered either simultaneously alongside the bronchoscope or after the bronchoscope has been placed at the selected site within the patient's lung.

Figure 21:
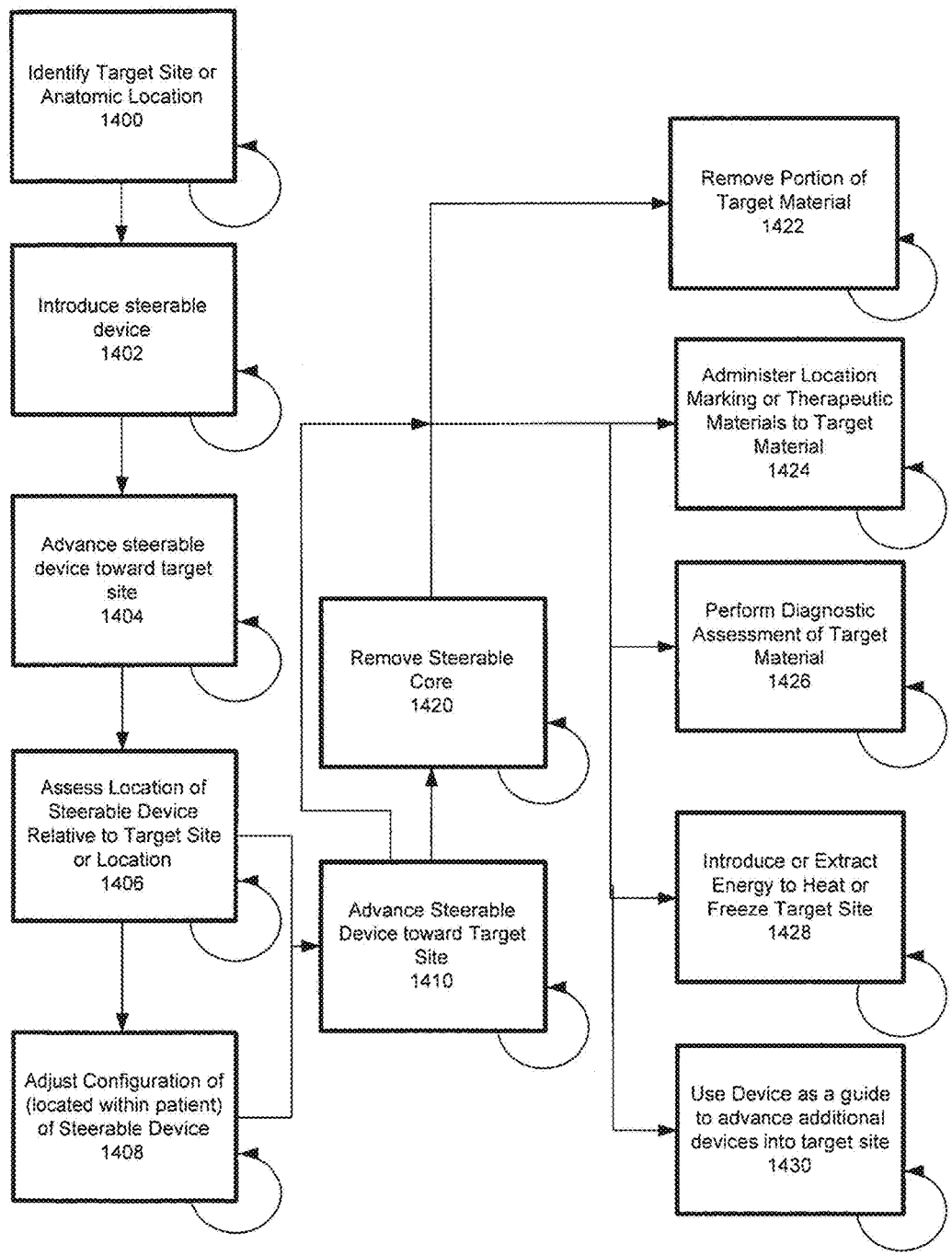
FIG. 21 illustrates the steps of a method for deploying the devices described herein.

FIG. 21 illustrates the steps of a method for operating and deploying the devices described herein. In a first step target site is identified 1400 in a patient. Once the target site is identified 1400, a steerable device is introduced 1402. The introduction of the steerable device 1402, is typically at a location that provides the most direct, unimpeded access to tissue. However, as will be appreciated by those skilled in the art, due to anatomical obstacles, the path may not necessarily present the shortest distance to the target site. Movement of the access point to a different location, which has a longer path to the target site, may be employed if desirable. For example, where dense tissue, or bones would impede the ability of the steerable device to reach its projected location, steering would be required.

Once the tissue has been identified and the steerable device has been introduced, the device is advanced toward the target site 1404. As discussed above, the entire device can be advanced (for example, the outer sheath and the steerable member) or just a component can be advanced. At some point while advancing the to the target site, it may be desirable to stop advancing the device, or to assess the location of the distal tip of the device relative to the target site 1406. The assessment can be done by obtaining a series of images, or as technology continues to develop by assessing the location and steering of the device relative to the target site real time, or near real time using available imaging techniques. Once the location of the distal tip of the steerable device is assessed, the configuration of the distal end of the steerable device can be configured 1408 to direct the steerable device to the target site (e.g. where the trajectory of the steerable device no longer intersects with the location of the target site). The steerable device is advanced to the target 1410, either with adjustment of the distal tip, or without, as desired.

Once the distal tip of the steerable device is positioned at the target site, the user can remove the steerable core (where a removable steerable core is provided) 1420 and replace the core with a tissue removal device 1422, a therapy delivery or location marking device 1424, or a diagnostic assessment device 1426 or introduce or extract energy to heat or freeze the target site 1428 or use a device as a guide to advance or deliver additional device to the target site 1430. As will be appreciated by those skilled in the art, each of the processes illustrated can be repeated (as indicated by the circular arrow path) and combinations of the steps can be practiced during a single session with a patient without departing from the scope of the invention. Steering mechanisms may be incorporated in therapy, treatment, diagnostic or• marking devices.

The steerable device can be used in combination with a number of devices to deliver therapy and/or diagnostics. See, for example, U.S. Pat. No. 6,945,942 entitled Device for Biopsy and Treatment of Breast Tumors (Van Bladel et al.); U.S. Pat. No. 6,789,545 entitled Method and System for Cryoablating Fibrodenomas (Littrup et al.); U.S. Pat. No. 6,551,255 entitled Device for Biopsy of Tumors (Van Bladel et al.); U.S. Pat. No. 5,916,212 entitled Hand Held Cryosurgical Probe System (Baust et al.); U.S. Pat. No. 5,846,235 entitled Endoscopic Cryospray Device (Pasricha et al.); U.S. Pat. No. 5,514,536 entitled Solutions for Tissue Preservation and Bloodless Surgery and Methods Using Same (Taylor); U.S. Pat. No. 5,978,697 entitled System and Method for MRI-Guided Cryosurgery (Ma al et al.); U.S. Pat. No. 6,875,209 entitled Cryoplasty Apparatus and Method (Zvuloni et al.); U.S. Pat. No. 6,962,587 entitled Method for Detecting and Treating Tumors Using Localized Impedance Measurement (Johnson et al.); U.S. Pat. No. 6,663,624 entitled RF Treatment Apparatus (Edwards et al.); U.S. Pat. No. 6,652,516 entitled Cell Necrosis Apparatus (Gough); U.S. Pat. No. 6,632,222 entitled Tissue Ablation Apparatus (Edwards et al.); U.S. Pat. No. 5,334,183 entitled Endoscopic Electrosurgical Apparatus (Wuchinich); U.S. Pat. No. 5,312,329 entitled Piezo Ultrasonic and Electrosurgical Handpiece (Beaty et al.); U.S. Pat. No. 6,752,767 entitled Localization Element with. Energized Tip (Turovskiy et al.); U.S. Pat. No. 6,652,520 entitled Modular Biopsy and Microwave Ablation Needle Delivery Apparatus Adapted to In Situ Assembly and Method of Use (Moorman et al.); U.S. Pat. No. 6,807,446 entitled Monopole Phased Array Thermotherapy Applicator for Deep Tumor Therapy (Penn et al.); U.S. Pat. No. 6,690,976 entitled Thermotherapy Method for Treatment and Prevention of Breast Cancer and Cancer in Other Organs (Penn et al.); U.S. Pat. No. 6,537,195 entitled Combination X-Ray Radiation and Drug Delivery Devices and Methods for Inhibiting Hyperplasia; U.S. Pat. No. 6,390,967 entitled Radiation for Inhibiting Hyperplasia After Intravascular Interfention (Forman et al.); U.S. Pat. No. 6,840,948 entitled Device for Removal of Tissue Lesions (Albrecht et al.); U.S. Pat. No. 6,942,627 entitled Surgical Biopsy Device Having a Flexible Cutter (Huitema); U.S. Pat. No. 6,758,824 entitled Biopsy Apparatus (Miller et al.); U.S. Pat. No. 6,312,428 entitled Methods and Apparatus for Therapeutic Cauterization of Predetermined Volumes of Biological Tissue (Eggers et al.); U.S. Pat. No. 6,287,304 entitled Interstitial Cautherization of Tissue Volumes with Electrosurgically Deployed Electrodes (Eggers et al.); U.S. Pat. No. 6,936,014 entitled Devices and Methods for Performing Procedures on a Breast (Vetter et al.); U.S. Pat. No. 6,863,676 entitled Excisional Biopsy Devices and Methods (Lee et al.); and U.S. Pat. No. 4,479,792 entitled Peritoneal Fluid Treatment Apparatus, Package and Method (Lazarus et al.).

Other devices that can be modified to incorporate the designs and objectives of the invention include steerable needle, lancet, trocar, stylet, cannula, device and/or system. See, U.S. Pat. No. 4,013,080 entitled Cannula Connector and Director Indicator Means for Injection System (Froning); U.S. Pat. No. 4,769,017 entitled Self-Sealing Infusion Manifold and Catheter Connector (Path et al); U.S. Pat. No. 5,240,011 entitled Motorized Biopsy Needle Positioner (Assa); U.S. Pat. No. 5,526,821 entitled Biopsy Needle with Sample Retaining Means (Jamshidi); U.S. Pat. No. 5,660,185 entitled Image-Guided Biopsy Apparatus with Enhanced Imaging and Methods (Shmulewitz); U.S. Pat. No. 5,735,264 entitled Motorized Mammographic Biopsy Apparatus (Siczek et al); U.S. Pat. No. 6,315,737 B1 entitled Biopsy Needle for a Biopsy Instrument (Skinner); U.S. Pat. No. 6,328,701 B1 entitled Biopsy Needle and Surgical Instrument (Terwilliger); U.S. Pat. No. 6,402,701 B1 entitled Biopsy Needle Instrument (Kaplan); U.S. Pat. No. 6,464,648 B1 entitled Biopsy Device and Remote Control Device Therefor (Nakamura); U.S. Pat. No. 6,485,436 B1 entitled Pressure-Assisted Biopsy Needle Apparatus and Technique (Truckai et al); U.S. Pat. No. 6,558,337 B2 entitled Positioner for Medical Devices such as Biopsy Needles (Dvorak et al); U.S. Pat. No. 6,709,408 B2 entitled Dual Action Aspiration Biopsy Needle (Fisher); U.S. Pat. No. 6,908,440 B2 entitled Dual Action Aspiration Biopsy Needle (Fisher); and U.S. Pat. No. 6,918,881 B2 entitled Biopsy Needle with Integrated Guide Pin (Miller et al). U.S. Patent Publications US 2004/0133168 A1 entitled Steerable Needle (Salcudean et al.); as well as PCT Publications WO 00/13592 A1 entitled Device for Receiving and Actuating a Biopsy Needle (Heinrich); WO 03/077768 A1 entitled Biopsy Needle and Biopsy Needle Module that Can be Inserted into the Biopsy Device (Heske et al); WO 2004/062505 A1 entitled Flexible Biopsy Needle (Bates et al.); and WO 2004/086977 A1 entitled Coaxial Cannula Provided with a Sealing Element (Heske et al.).

In addition to the use of scopes to introduce the steerable needles, lancets, trocars, stylets, cannulas, devices and/or systems of the invention, a variety of other techniques are also suitable for inserting the steerable devices of the invention into a patient. One such suitable technique is the Seldinger technique, developed by the Swedish radiologist Sven-Ivar Seldinger to provide a method for percutaneous puncture and catheterization of the arterial system. The Seldinger technique employs the use of a thin walled percutaneous device, such as a needle, to access a patient. A guidewire is passed through the lumen of the needle. The guidewire is advanced into the tissue (beyond the distal end of the needle) and the needle is withdrawn. At that point, the puncture site (where the needle and guidewire entered the patient) can be enlarged, if desired. An outer sheath (such as those described above) is then advanced over the guidewire toward the target site. After the outer sheath is positioned, the guidewire is removed and the steerable member is inserted. Thereafter the entire system can be advanced toward the target site directly or employing any of the steering mechanisms described above. This technique, and modifications that take into consideration the device and systems designs of this invention, can also be employed.

An additional application of the device includes the accurate delivery of materials to a target site. Materials includes: therapeutic and diagnostic substances, in liquid, solid, or any other form. For example, agents suitable for chemical pleurodesis, including radioactive isotopes, tetracycline, chemotherapeutic agents, and talc can be delivered using the devices and techniques of the invention.

In another application of the device and methods, accurate delivery of materials to a target site, includes the delivery of adhesive materials, such as those having strength values up to 1.5 psi, or more; preferably having a strength value between 0.2-0.6 psi. In addition, the adhesive material suitable for any of the embodiments of the methods of the invention have viscosity levels of 1.1 centipoise and higher. Further, materials suitable for performing any of the methods of the invention can be selected from the group comprising hydrogels, proteins, polymers and cross-linking agents. The hydrogel adhesive may include material selected from the group consisting of hyalurons, hyaluronic acid, alginates, chitins, chitosans, and derivatives thereof. The protein material comprises material that can be selected from the group consisting of albumins, porcine albumin, collagens and gelatins. The polymer material comprises material selected from the group consisting of poly(lactic acid) and poly(glycolide). The cross-linking agent material comprises material that may be selected from the group consisting of glutaraldehyde and stable polyaldehyde. For example, adhesive material could be delivered to a target site and allowed to cure at the location of a small lesion. The curing of the material would provide in situ a lump of material having a consistency different from natural tissue that a surgeon could then use to determine the location of the target lesion. Determination of the location of the material could be determined by palpation. In another embodiment, an inner member could surround the tissue and a polymerizing adhesive material could be extruded from between an outer member and the inner member, the extrusion could be performed as the device were drawn out, thereby forming a sheath around the target site and encapsulating it. The encapsulated tissue, now prevented from obtaining nourishment from blood flow, would then become necrotic and could be removed in a subsequent procedure. For example, where a patient is undergoing chemotherapy and has a compromised immune system, it may be desirable to encapsulate target lesions and then, after the patient has recovered from the chemotherapy, remove the encapsulated lesions.

Although many alternative sealant formulations may be suitable for the purposes described herein, a preferred sealant would consist of primarily a combination of stable polyaldehyde, albumin and collagen with or without additional additives. The sealant can also have agents that initiate or accelerate the clotting cascade so the sealant can be used as a hemostatic agent. For example, a suitable material is described in US Patent Application Publ. No. 2004/0081676. The glue's intrinsic viscosity can be tuned to allow for fast or slow delivery through a delivery system and includes glue viscosity more than 1.1 centipoise. This glue formulation is appropriate for use with all lung tissue and structures within the pulmonary system as well as pulmonary vasculature. It can also be formulated and used for any adhesive or anti-adhesion purpose including anastomosis of blood vessels and bronchi/bronchioles and to seal pulmonary structures from air leaks, bleeding or fluid leaks. Ideally, the sealant will cure within a few minutes, works well in a damp or wet environment, and blocks air or fluid from entering the pleural cavity. Typically, the glues are composed of a condensation product of glutaraldehyde that consists of cross-linked albumin, including porcine albumin. Adhesion values for the glue can be up to 1.5 psi, more preferably between 0.2-0.6 psi. Agents can be included in the adhesives that absorb x-rays to enhance the ability to visualize the target site.

Still another application of the device and methods provides for the accurate delivery of therapeutic materials, such as chemotherapy agents, and biologically active agents, to a target site. Yet another application of the device and methods provides for the accurate delivery of therapeutic materials, such as chemotherapy agents, and biologically active agents, to a target site using a delivery medium. For example, therapeutic materials can be incorporated into a material being delivered, such as glue. The therapeutic material can be incorporated into the material to provide time-released delivery of the therapeutic material.

Yet another application of the device and method provides for the accurate delivery using a steerable device of bioabsorbable materials or drug delivery materials (e.g. a drug eluting delivery device). For example, it may be desirable to deliver all, or a part of the material to be delivered in bioresorbable polymers. Bioresorbable materials are those materials made from essentially the same lactic acid molecular building blocks that occur naturally in the human body. Long polymer chains are created to form polylactides (PLa). Thus for example, a biologically and biomechanically active PLa can be delivered using the steerable device which is then resorbed during the healing process.

In still other embodiments, biocompatible polymers, biocompatible foams, such thermoplastic syntactic foam, water-insoluble derivatives of hyaluronic acid in the form of gels, films and sponges, polyglycolic acid, low-density reticulated vitreous carbon (RVC), and hydrogels can be delivered using the steerable devices of the invention. The materials delivered can be prepared in colored form by including a dye or stain to assist in easier handling and visualization during or after the process. The materials delivered can also be selected for its ability to become more or less viscous as the material approaches body temperature, or to provide growth factors, antibiotics, or other agents to the site. Materials may also be loaded with pharmaceutical agents which are delivered to the site by a permeable or semi-permeable membrane.

Kits employing the devices; components and materials of the invention can also be employed.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of delivering a device to a target site in a lung of a patient comprising:
   penetrating parietal pleura tissue and visceral pleura tissue of the patient with a steerable member;
   applying a bending force after penetrating the parietal pleura tissue and visceral pleura tissue of the patient to bend the steerable member to access the target site in the lung of the patient; and
   delivering the device to the target site in the lung of the patient.

2. The method of claim 1 further comprising the step of using the steerable member to advance another device to the target site.

3. The method of claim 1 further comprising the step of distally advancing the steerable member through the tissue so as to angle a path away form an axial trajectory defined by the steerable member to deliver the device to the target site.

4. The method of claim 1 wherein the step of applying a bending force further comprises bending a bendable portion of the steering member while the bendable portion of the steering member is positioned within tissue.

5. The method of claim 1 further comprising the step of aspirating at the target site.

6. The method of claim 1 further comprising the step of removing tissue at the target site.

7. The method of claim 1 further comprising the step of draining the target site.

8. The method of claim 1 further comprising the step of infusing the target site with a therapeutic or diagnostic material.

9. The method of claim 1 further comprising the step of delivering energy to the target site.

10. The method of claim 1 further comprising the step of extracting heat energy from the target site.

11. The method of claim 1 further comprising the step of killing tissue at the target site.

12. A method of delivering a device to a target site in a lung of a patient comprising:
    penetrating parietal pleura tissue and visceral pleura tissue of the patient with a steerable member;
    actively changing a shape of the steerable member after penetrating the parietal pleura tissue and visceral pleura tissue of the patient to access the target site in the lung of the patient; and
    delivering the device to the target site in the lung of the patient.

* * * * *